United States Patent
Giencke et al.

[11] Patent Number: 6,071,860
[45] Date of Patent: *Jun. 6, 2000

[54] 2,4-DIAMINO-1, 3,5-TRIAZINES, THEIR PREPARATION, AND THEIR USE AS HERBICIDES AND PLANT GROWTH REGULATORS

[75] Inventors: Wolfgang Giencke; Lothar Willms, both of Hofheim; Klaus Bauer, Hanau; Hermann Bieringer, Eppstein; Christopher Rosinger, Hofheim, all of Germany

[73] Assignee: Hoechst Schering AgrEvo GmbH, Berlin, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/796,398

[22] Filed: Feb. 6, 1997

[30] Foreign Application Priority Data

Feb. 6, 1996 [DE] Germany .......................... 196 04 191

[51] Int. Cl.$^7$ ...................... C07D 251/70; C07D 401/12; A01N 43/68

[52] U.S. Cl. .......................... 504/232; 504/233; 504/234; 504/228; 504/225; 504/221; 504/222; 504/223; 544/206; 544/207; 544/113; 544/51; 544/52; 544/48; 544/183; 544/91; 544/105

[58] Field of Search .................... 544/206, 207, 544/113, 51, 52, 48, 91, 105; 504/232, 228, 225, 221, 222, 223, 233, 234

[56] References Cited

U.S. PATENT DOCUMENTS

| | | | |
|---|---|---|---|
| 3,816,419 | 6/1974 | Cross | 260/249.9 |
| 3,821,228 | 6/1974 | Richards | 260/288 |
| 3,829,573 | 8/1974 | Richards | 424/250 |
| 3,899,490 | 8/1975 | Richards | 260/268 |
| 3,929,784 | 12/1975 | Richards | 260/247.5 |
| 4,833,169 | 5/1989 | Von Sprecker | 514/530 |
| 4,932,998 | 6/1990 | Takematsu | 544/207 |
| 5,130,339 | 7/1992 | Cecchi et al. | 514/653 |
| 5,137,901 | 8/1992 | Junge et al. | 514/373 |
| 5,290,754 | 3/1994 | Nishii | 504/232 |
| 5,296,482 | 3/1994 | Peglion et al. | 514/213 |
| 5,403,815 | 4/1995 | Nishii | 504/230 |
| 5,527,954 | 6/1996 | Adachi | 560/227 |
| 5,541,343 | 7/1996 | Himmelsbach et al. | 514/424 |
| 5,573,949 | 11/1996 | Cecchi et al. | 435/280 |
| 5,591,769 | 1/1997 | Himmeslbach et al. | 514/423 |

FOREIGN PATENT DOCUMENTS

| | | |
|---|---|---|
| 2179205 | 12/1996 | Canada . |
| 0043194 | 1/1982 | European Pat. Off. . |
| 0213080 | 3/1987 | European Pat. Off. . |
| 0283522 | 9/1988 | European Pat. Off. . |
| 0338793 | 10/1989 | European Pat. Off. . |
| 0352613 | 1/1990 | European Pat. Off. . |
| 0361577 | 4/1990 | European Pat. Off. . |
| 0411153 | 2/1991 | European Pat. Off. . |
| 0436435 | 7/1991 | European Pat. Off. . |
| 0483667 | 5/1992 | European Pat. Off. . |
| 0 509 544 | 10/1992 | European Pat. Off. . |
| 0534859 | 3/1993 | European Pat. Off. . |
| 0589037 | 3/1994 | European Pat. Off. . |
| 0620220 | 10/1994 | European Pat. Off. . |
| 0 492 615 | 3/1995 | European Pat. Off. . |
| 0661274 | 7/1995 | European Pat. Off. . |
| 0678579 | 10/1995 | European Pat. Off. . |
| 0683236 | 11/1995 | European Pat. Off. . |
| 0749970 | 12/1996 | European Pat. Off. . |
| 2 000 204 | 8/1969 | France . |
| 195 22 137 | 1/1997 | Germany . |
| 485647 | 2/1970 | Switzerland . |
| 1166538 | 10/1969 | United Kingdom . |
| WO88/02368 | 4/1988 | WIPO . |
| WO90/09378 | 8/1990 | WIPO . |
| WO90/24086 | 10/1994 | WIPO . |
| WO 95/08527 | 3/1995 | WIPO . |
| WO 95/24393 | 9/1995 | WIPO . |

OTHER PUBLICATIONS

Database WPI, Week 9628, Derwent Publications Ltd. AN 96–272740, XP002030579. No Date.
Chemical Abstracts, vol. 92, No. 9, Mar. 3, 1980, AN 69219v, XP002030574, Bd. 9, Nr. 5, 1979, pp. 323–332.
Chemical Abstracts, vol. 92, No. 23, Jun. 9, 1980, AN XP002030575, Bd. 23, Nr. 5, 1980, pp. 502–505.
Chemical Abstracts, vol. 87, No. 5, Aug. 1, 1997, AN 33435v, XP002030576, Bd. 20, No. 6, 1977, pp. 771–776.
Chemical Abstracts, vol. 85, No. 17, Oct. 25, 1976, AN 122909d, XP002030577, pp. 103–104.
Chemical Abstracts, vol. 70, No. 1, Jan. 6, 1969, AN 3950r, XP002030578.
Takematsu et al., Chemical Abstracts, vol. III, Entry 115214a (1989).

*Primary Examiner*—John M. Ford
*Attorney, Agent, or Firm*—Frommer Lawrence & Haug LLP

[57] ABSTRACT

Compounds of the formula (I) and salts thereof

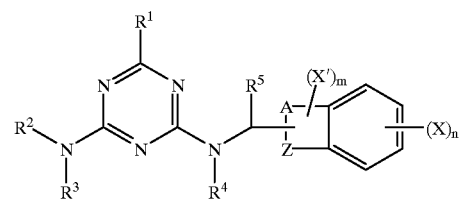

(I)

where
$R^1$ to $R^5$, A, Z, X, X', n and m are as defined in claim 1 are suitable as herbicides and plant growth regulators. They can be prepared analogously to known processes using novel intermediates of the formula (V)

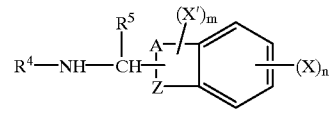

(V)

25 Claims, No Drawings

2,4-DIAMINO-1, 3,5-TRIAZINES, THEIR PREPARATION, AND THEIR USE AS HERBICIDES AND PLANT GROWTH REGULATORS

The invention is in the technical field of the herbicides and plant growth regulators, in particular of the herbicides for selective control of broad-leaved and grass weeds in crops of useful plants.

It has been disclosed that 2-amino-4-(phenoxyalkylamino)-1,3,5-triazines which are substituted in the 6-position have herbicidal and plant growth-regulating properties; cf. WO 94/24086, EP-A-509544, EP-A492615. There have furthermore already been disclosed 2-amino-4-[arylamino- or (hetero)arylalkylamino]-haloalkyl-1,3,5-triazines which are herbicidally active; cf. U.S. Pat. No. 3,816,419, WO 90109378, WO 88/02368.

The prior-art active substances which have a 4-[(hetero)arylalkylamino] group contain, as the "alkyl", in each case a methylene bridge which is optionally additionally with or without a branching substituent.

Upon use, the prior-art active substances have disadvantages in some cases, be it an insufficient herbicidal activity against harmful plants, too narrow a spectrum of harmful plants which can be controlled with an active substance, or not enough selectivity in crops of useful plants. Other active substances cannot be produced economically on an industrial scale due to reagents and precursors which are not readily accessible, or lack sufficient chemical stability.

The object of the invention is to provide alternative active substances of the type of the 2,4-diamino-1,3,5-triazines which can be employed as herbicides or plant growth regulators.

German Patent Application No. 19 522 137.0 proposes, inter alia, herbicides of the abovementioned type which contain, in the 6-position on the triazine ring, an optionally substituted cycloalkyl radical or a heterocycle with an oxygen, nitrogen or sulfur atom and, in the 4-position, a phenylalkyl radical with a linear propylene bridge which is optionally additionally with or without a branching substituent.

The present invention relates to compounds of the formula (I) and to salts thereof

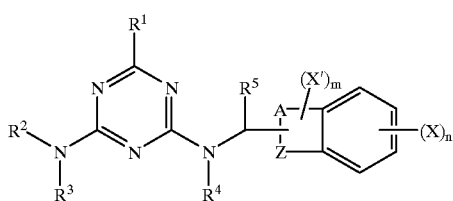

(I)

in which $R^1$ is $(C_1-C_6)$alkyl
which is unsubstituted or substituted by one or more radicals selected from the group consisting of halogen, cyano, nitro, thiocyanato, hydroxyl, $(C_1-C_4)$alkoxy, $(C_1-C_4)$alkylthio, $(C_1-C_4)$alkylsulfinyl, $(C_1-C_4)$alkylsulfonyl, $(C_2-C_4)$alkenyl, $(C_2-C_4)$alkynyl, phenyl which is unsubstituted or substituted, $(C_3-C_9)$cycloalkyl which is unsubstituted or substituted, and heterocyclyl having 3 to 6 ring atoms and 1 to 3 hetero ring atoms selected from the group consisting of N, O and S, the ring being unsubstituted or substituted, or
a carbocyclic or heterocyclic radical having 3 to 6 ring atoms which is unsubstituted or substituted by one or more radicals selected from the group consisting of halogen, nitro, cyano, thiocyanato and a radical of the formula $B^1—Y^1$, where $B^1$ and $Y^1$ are as defined further below, it also being possible for pairs of substituents to form a carbocyclic or heterocyclic ring having 3 to 6 ring atoms which is unsubstituted or substituted, preferably $R^1$ is a radical having in total 1 to 20 carbon atoms, in particular I to 10 carbon atoms, $R^2$ and $R^3$ are in each case independently of one another hydrogen, amino, alkylamino or dialkylamino, each of which has 1 to 6 carbon atoms in the alkyl radical, an acyclic or cyclic hydrocarbon radical or hydrocarbon-oxy radical having in each case 1 to 10 carbon atoms, preferably 1 to 6 carbon atoms, or a heterocyclyl radical, heterocyclyloxy radical or heterocyclylamino radical having in each case 3 to 6 ring atoms and 1 to 3 hetero ring atoms selected from the group consisting of N, O and S, each of the five last-mentioned radicals being unsubstituted or substituted, or an acyl radical, or $R^2$ and $R^3$ together with the nitrogen atom of the group $NR^2R^3$ are a heterocyclic radical having 3 to 6 ring atoms and 1 to 4 hetero ring atoms, where, besides the nitrogen atom, the optional further hetero ring atoms are selected from the group consisting of N, O and S and the radical is unsubstituted or substituted, $R^4$ is hydrogen, amino, alkylamino or dialkylamino, each of which has 1 to 6 carbon atoms in the alkyl radical, an acyclic or cyclic hydrocarbon radical or hydrocarbon-oxy radical having in each case 1 to 10 carbon atoms, preferably 1 to 6 carbon atoms, or a heterocyclyl radical, heterocyclyloxy radical or heterocyclylamino radical having in each case 3 to 6 ring atoms and 1 to 3 hetero ring atoms selected from the group consisting of N, O and S, each of the five last-mentioned radicals being unsubstituted or substituted, or an acyl radical, $R^5$ is hydrogen, nitro, cyano, thiocyanato or a radical of the formula $—B^2—Y^2$, where $B^2$ and $Y^2$ are as defined further below, A-Z is a divalent bridge of the formula

| | |
|---|---|
| $—(CH_2)_a—$, | where a is the integer 2, 3 or 4, |
| $—W^1—(CH_2)_b—W^2—$, | where b is the integer 1 or 2 and $W^1$, $W^2$ independently of one another are NR, O or S, |
| $—CH_2CH_2CH_2—W^3—$, | where $W^3$ is NR, O or S, |
| $—W^4—CH=CH—W^5—$, | Where $W^4$, $W^5$ independently of one another are NR, O or S, |
| $—CH=CH—CH_2—W^6—$, | where $W^6$ is a group of the formula NR, O or S, or |
| $—CH_2CH_2NR—$, | |
| $—W^7—CH=N—$, | where $W^7$ is a group NR, O, or S, |
| $—W^8CH_2—N=N—$, | where $W^8$ is a group NR, O or S, |
| $—CH=CH—N=N—$, | |
| $—N=CH—CH=N—$, | |
| $—CH=CH—CH_2—$, | |
| $—CH=CH—CH=CH—$ or | |
| $—CH=CH—NR—$ | | where R in the abovementioned groups NR is in each case H or $(C_1-C_4)$alkyl, $(X')_m$ denotes m substituents X' where the X' in each case independently of one another are halogen, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $[(C_1-C_4)$alkyl$]$ carbonyl, $[(C_1-C_4)$alkoxy$]$carbonyl or $[(C_1-C_4)$ alkylthio$]$-carbonyl, the hydrocarbon-containing moieties in the last-mentioned 9 radicals being unsubstituted or substituted, or the oxo group, $(X)_n$ denotes n substituents X where the X in each case independently of one another are halogen, nitro, cyano, $(C_1-C_6)$alkyl, $(C_2-C_6)$alkenyl, $(C_2-C_6)$alkynyl, $(C_1-C_6)$ alkoxy, $(C_2-C_6)$alkenyloxy, $(C_2-C_6)$alkynyloxy, $[(C_1-C_4)$ alkyl]carbonyl, $[(C_1-C_4)$alkoxy]carbonyl or $[(C_1-C_4)$ alkylthio]carbonyl, where the hydrocarbon-containing moities in the last-mentioned 9 radicals are unsubstituted or substituted, or a radical of the formula $—B^3—Y^3$, where $B^3$ and $Y^3$ are as defined below, or two adjacent radicals X together are a fused cycle having 4 to 6 ring atoms which is carbocyclic or contains hetero ring atoms from the group consisting of O, S and N and which is unsubstituted or substituted by one or more radicals selected from the group consisting of halogen, $(C_1-C_4)$alkyl and oxo, $B^1, B^2, B^3$ in each case independently of one another are a direct bond or a divalent group of the formula —O—, $—S(O)_p—$, $—S(O)_p—O—$, $—O—S(O)_p—$, —CO—, —O—CO—, —CO—O—, —NR'—, —O—NR'—, —NR'—O—, —NR'—CO— or —CO—NR'—, where p=0, 1 or 2 and R' is hydrogen, alkyl having 1 to 6 carbon atoms, phenyl, benzyl, cycloalkyl having 3 to 6 carbon atoms or alkanoyl having 1 to 6 carbon atoms, $Y^1, Y^2$ in each case independently of one another are H or an acyclic hydrocarbon radical, for example having in each case 1 to 20 carbon atoms, preferably 1 to 10 carbon atoms, or a cyclic hydrocarbon radical having 3 to 8 carbon atoms, preferably 3 to 6 carbon atoms, or a heterocyclic radical having 3 to 9 ring atoms and 1 to 3 hetero ring atoms selected from the group consisting of N, O and S, each of the three last-mentioned radicals being unsubstituted or substituted, $Y^3$ is an aromatic, saturated or partially saturated carbocyclic or heterocyclic radical, the cyclic radical being substituted or unsubstituted, m is an integer from zero up to the number of the hydrogen atoms in the skeleton of the divalent bridge, preferably 0, 1 or 2, in particular 0, n is 0, 1, 2, 3 or 4, preferably 0, 1 or 2.

The compounds of the formula (I) can form salts by subjecting a suitable inorganic or organic acid, for example HCl, HBr, $H_2SO_4$ or $HNO_3$, but also oxalic acid or sulfonic acids, to an addition reaction with a basic group, for example amino or alkylamino. Suitable substituents which are in deprotonated form, for example sulfonic acids or carboxylic acids, can form internal salts with groups which are protonizable in turn, such as amino groups. Salts can also be formed by replacing the hydrogen in suitable substituents, for example sulfonic acids or carboxylic acids, by a cation which is suitable for agriculture. Examples of these salts are metal salts, in particular alkali metal salts or alkaline earth metal salts, in particular sodium and potassium salts, or else ammonium salts or salts with organic amines.

In formula (I) and in all subsequent formulae, the radicals alkyl, alkoxy, haloalkyl, haloalkoxy, alkylamino and alkylthio and the corresponding unsaturated and/or saturated radicals in the hydrocarbon skeleton can in each case be straight-chain or branched. Unless specifically indicated, the lower hydrocarbon skeletons, for example those having 1 to 6 carbon atoms, or in the case of unsaturated groups, 2 to 6 carbon atoms, are preferred amongst these radicals. Alkyl radicals, also in the composite meanings of alkoxy, haloalkyl and the like, are, for example, methyl, ethyl, n- or i-propyl, n-, i-, t- or 2-butyl, pentyl radicals, hexyl radicals, such as n-hexyl, i-hexyl and 1,3-dimethylbutyl, heptyl radicals, such as n-heptyl, 1-methylhexyl and 1,4-dimethylpentyl; alkenyl and alkynyl radicals have the meanings of the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Alkenyl in the form of $(C_3-C_4)$alkenyl is preferably an alkenyl radical having 3 or 4 carbon atoms in which the multiple bond is not between C-1 and C-2, C-1 being the carbon atom in the position of "yl". This also applies analogously to $(C_3-C_4)$alkynyl.

Cycloalkyl is a carbocyclic saturated ring system having preferably 3–8 carbon atoms, e.g. cyclopropyl, cyclopentyl or cyclohexyl.

Halogen is, for example, fluorine, chlorine, bromine or iodine. Haloalkyl, -alkenyl and -alkynyl are alkyl, alkenyl or alkynyl which are partially or fully substituted by halogen, preferably by fluorine, chlorine and/or bromine, in particular by fluorine or chlorine, for example monohaloalkyl (=monohalogenoalkyl), perhaloalkyl, $CF_3$, $CHF_2$, $CH_2F$, $CF_3CF_2$, $CH_2FCHCl$, $CH_2CF_3$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl and other halogen-substituted radicals.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl in this context is a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl; this also applies analogously to a hydrocarbon radical in a hydrocarbon-oxy radical.

A heterocyclic radical or ring (heterocyclyl) can be saturated, unsaturated or heteroaromatic; preferably, it contains one or more hetero units in the ring, i.e. hetero atoms or ring members which also include substituted hetero atoms, preferably selected from the group consisting of N, O, S, SO, $SO_2$; it is preferably an aliphatic heterocyclyl radical having 3 to 7 ring atoms or a heteroaromatic radical having 5 or 6 ring atoms and contains 1, 2 or 3 hetero units. The heterocyclic radical can be, for example, a heteroaromatic radical or ring (heteroaryl), for example a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or it is a partially or fully hydrogenated radical such as oxiranyl, pyrrolidyl, piperidyl, piperazinyl, dioxolanyl, morpholinyl, tetrahydrofuryl. Substituents which are suitable for a substituted heterocyclic radical are the substituents mentioned further below and additionally also oxo. The oxo group can also occur on the hetero ring atoms which may exist at various oxidation levels, for example on N and S. Substituted radicals, such as substituted hydrocarbon radicals, for example substituted alkyl, alkenyl, alkynyl, aryl, phenyl and benzyl, or substituted heterocyclyl or heteroaryl are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxy, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl; the term "substituted radicals", such as substituted alkyl and the like, includes, as substituents, in addition to the abovementioned saturated hydrocarbon-containing radicals the corresponding unsaturated aliphatic and aromatic radicals, such as optionally substituted alkenyl, alkynyl, alkenyloxy, alkynyloxy, phenyl, phenoxy and the like. Preferred amongst radicals having carbon atoms are those having 1 to 4 carbon atoms, in particular 1 or 2 carbon atoms. Preferred are, as a rule, substituents selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Especially preferred in this context are the substituents methyl, methoxy and chlorine.

Mono- or disubstituted amino is a chemically stable radical selected from the group consisting of the substituted amino radicals which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred in this context are alkyl radicals having 1 to 4 carbon atoms; aryl is in this context preferably phenyl or substituted phenyl; acyl is as defined further below, preferably $(C_1-C_4)$alkanoyl. This also applies analogously to substituted hydroxylamino or hydrazino.

Optionally substituted phenyl is preferably phenyl which is unsubstituted or mono- or polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid, and radicals of acids derived therefrom, such as thiocarboxylic acid, optionally N-substituted iminocarboxylic acids, or the radical of carbonic monoesters, of optionally N-substituted carbamic acid, of sulfonic acids, sulfinic acids, phosphonic acids and phosphinic acids. Acyl is, for example, formyl, alkylcarbonyl, such as $[(C_1-C_4)$alkyl$]$carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals can in each case be further substituted in the alkyl or phenyl moiety, for example in the alkyl moiety by one or more radicals selected from the group consisting of halogen, alkoxy, phenyl and phenoxy; examples of substituents in the phenyl moiety are these which have already been generally mentioned further above for substituted phenyl.

The invention also relates to all stereoisomers embraced by formula (I) and to mixtures of these. Such compounds of the formula (I) contain one or more asymmetric carbon atoms or else double bonds which are not mentioned separately in formula (I). Formula (I) embraces all possible stereoisomers which are defined by their specific spatial form, such as enantiomers, diastereomers and Z and E isomers; they can be obtained from mixtures of the stereoisomers by customary methods or prepared by stereoselective reactions in combination with the use of stereochemically pure starting materials.

Compounds of the abovementioned formula (I) according to the invention or their salts which are of particular interest, mainly for reasons of a higher herbicidal activity, better selectivity and/or better properties when being prepared are those in which $R^1$ is $(C_1-C_4)$alkyl,
which is unsubstituted or substituted by one or more radicals selected from the group consisting of halogen, $(C_1-C_4)$alkoxy, $(C_1-C_4)$alkylthio, $(C_1-C_4)$alkylsulfonyl, phenyl which is unsubstituted or substituted by one or more radicals selected from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, amino, mono- and di$[(C_1-C_4)$alkyl$]$amino, $(C_1-C_4)$alkanoylamino, benzoylamino, nitro, cyano, $[(C_1-C_4)$alkyl$]$carbonyl, formyl, carbamoyl, mono- and di-$[(C_1-C_4)$alkyl$]$aminocarbonyl and $(C_1-C_4)$alkylsulfonyl, and $(C_3-C_9)$cycloalkyl which is unsubstituted or substituted by one or more radicals $(C_1-C_4)$alkyl, and heterocyclyl having 3 to 6 ring atoms and 1 to 3 hetero ring atoms selected from the group consisting of N, O and S, the ring being unsubstituted or substituted by one or more radicals selected from the group consisting of halogen, $(C_1-C_4)$alkyl and oxo,
or
$(C_3-C_7)$cycloalkyl, $(C_3-C_7)$cycloalkenyl or a heterocyclic radical having 3 to 6 ring atoms and 1 to 3 hetero ring atoms selected from the group consisting of N, O and S, the cycloalkyl radical or the heterocyclic radical in each case being unsubstituted or substituted by one or more radicals selected from the group consisting of halogen, nitro, cyano, thiocyanato and a radical of the formula $B^1-Y^1$, where $B^1$ and $Y^1$ are as defined further below, and/or has substituents which, in pairs, can form a fused benzene ring or a fused or spiro-linked ring selected from the group consisting of $(C_3-C_7)$cycloalkyl, $(C_3-C_7)$cycloalkenyl and a heterocyclic ring having 3 to 6 ring atoms which is unsubstituted or substituted by one or more radicals selected from the group consisting of halogen, $(C_1-C_4)$alkyl, $(C_1-C_4)$haloalkyl and oxo, or phenyl which is unsubstituted or substituted, preferably $R^1$ is a radical having in total 1 to 20 carbon atoms, in particular 1 to 10 carbon atoms, $R^2$ and $R^3$ in each case independently of one another are hydrogen, amino or alkylamino or dialkylamino, each of which has 1 to 4 carbon atoms in the alkyl radical, an acyclic or cyclic hydrocarbon radical or hydrocarbon-oxy radical, each of which has 1 to 6 carbon atoms, or a heterocyclyl radical, heterocyclyloxy radical or heterocyclylamino radical, each of which has 3 to 6 ring atoms and 1 to 3 hetero ring atoms selected from the group consisting of N, O and S, where each of the five last-mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy$]$carbonyl, $[(C_1-C_4)$alkyl$]$carbonyl, formyl, carbamoyl, mono- and di$[(C_1-C_4)$alkyl$]$aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, or $R^2$ and $R^3$ together with the nitrogen atom of the group $NR^2R^3$ are a heterocyclic radical having 3 to 6 ring atoms and 1 to 2 hetero ring atoms where, besides the nitrogen atom, the optional other hetero ring atom is selected from the group consisting of N, O and S and the radical is unsubstituted or substituted by one or more radicals selected from the group consisting of halogen, $(C_1-C_4)$alkyl and oxo, $R^4$ is hydrogen, amino, alkylamino or dialkylamino, each of which has 1 to 6 carbon atoms in the alkyl radical, an acyclic or cyclic hydrocarbon radical or hydrocarbon-oxy radical, each of which has 1 to 6 carbon atoms, or a heterocyclyl radical, heterocyclyloxy radical or heterocyclylamino radical, each of which has 3 to 6 ring atoms and 1 to 3 hetero ring atoms selected from the group consisting of N, O and S, where each of the five last-mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, $R^5$ is hydrogen, nitro, cyano, thiocyanato or a radical of the formula $-B^2-Y^2$, where $B^2$ and $Y^2$ are as defined further below, A-Z is a divalent bridge of the formula

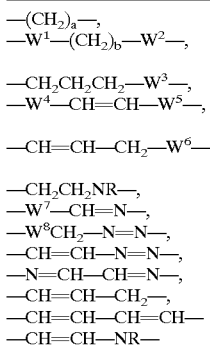

| | |
|---|---|
| $-(CH_2)_a-$, | where a is the integer 2, 3 or 4, |
| $-W^1-(CH_2)_b-W^2-$, | where b is the integer 1 or 2 and $W^1$, $W^2$ independently of one another are S or O, |
| $-CH_2CH_2CH_2-W^3-$, | where $W^3$ is NR, O or S, |
| $-W^4-CH=CH-W^5-$, | where $W^4$, $W^5$ independently of one another are S or O, |
| $-CH=CH-CH_2-W^6-$, | where $W^6$ is a group of the formula S or O, or |
| $-CH_2CH_2NR-$, | |
| $-W^7-CH=N-$, | where $W^7$ is a group NR, O or S, |
| $-W^8CH_2-N=N-$, | where $W^8$ is a group NR, O or S, |
| $-CH=CH-N=N-$, | |
| $-N=CH-CH=N-$, | |
| $-CH=CH-CH_2-$, | |
| $-CH=CH-CH=CH-$ | or |
| $-CH=CH-NR-$ | | where R in the groups NR is in each case H, methyl or ethyl, $(X')_m$ denotes m substituents $X'$ where the $X'$ in each case independently of one another are halogen, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $[(C_1-C_4)$alkyl]carbonyl, $[(C_1-C_4)$alkoxy]carbonyl or $[(C_1-C_4)$alkylthio]carbonyl, the hydrocarbon-containing moieties in the last-mentioned 9 radicals being unsubstituted or substituted by one or more radicals selected from the group consisting of halogen, $(C_1-C_4)$alkoxy and $(C_1-C_4)$alkylthio, or the oxo group, $(X)_n$ denotes n substituents X where the X in each case independently of one another are halogen, nitro, cyano, $(C_1-C_6)$alkyl, $(C_1-C_6)$alkoxy, $(C_1-C_4)$alkylcarbonyl, $(C_1-C_4)$alkyloxycarbonyl or $(C_1-C_4)$alkylthiocarbonyl, the last-mentioned five radicals being unsubstituted or substituted by halogen or $(C_1-C_4)$alkoxy, a radical of the formula $-B^3-Y^3$, where $B^3$ and $Y^3$ are as defined below, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$alkyl and oxo, $B^1$, $B^2$ and $B^3$ in each case independently of one another are a direct bond or a divalent group of the formula $-O-$, $-S-$, $-CO-$, $-O-CO-$, $-CO-O-$, $-NR'-$, $-NR'-CO-$ or $-CO-NR'-$, where R' is H or $(C_1-C_4)$alkyl, $Y^1$ and $Y^2$ in each case independently of one another are H or an acyclic hydrocarbon radical having 1 to 6 carbon atoms, a cyclic hydrocarbon radical having 3 to 6 carbon atoms or a heterocyclic radical having 3 to 9 ring atoms and 1 to 3 hetero ring atoms selected from the group consisting of N, O and S, each of the three last-mentioned radicals being unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, $Y^3$ is $(C_3-C_6)$cycloalkyl which is unsubstituted or substituted by radicals selected from the group consisting of $(C_1-C_4)$alkyl and $(C_1-C_4)$haloalkyl, or phenyl which is unsubstituted or substituted by radicals selected from the group consisting of halogen, $(C_1-C_4)$alkyl, $(C_1-C_4)$haloalkyl and $(C_1-C_4)$alkoxy, m is 0, 1 or 2, preferably 0 or 1, in particular 0, n is 0, 1, 2, 3 or 4, preferably 0, 1 or 2.

Of special interest are furthermore compounds of the formula (I) according to the invention and their salts in which $R^1$ is $(C_1-C_4)$alkyl, which is unsubstituted or substituted by one or more radicals selected from the group consisting of halogen, $(C_1-C_4)$alkoxy, $(C_1-C_4)$alkylthio and phenyl which is unsubstituted or substituted by one or more radicals selected from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, nitro, cyano, $[(C_1-C_2)$alkyl]carbonyl, formyl, carbamoyl, mono- and di$[(C_1-C_2)$alkyl]aminocarbonyl, $(C_1-C_4)$alkylsulfonyl and $(C_3-C_7)$cycloalkyl which is unsubstituted or substituted by one or more radicals $(C_1-C_4)$alkyl, or $(C_3-C_7)$cycloalkyl or a heterocyclic radical having 3 to 6 ring atoms and 1 or 2 hetero ring atoms selected from the group consisting of N, O and S, the cycloalkyl radical or the heterocyclic radical in each case being unsubstituted or substituted by one or more radicals selected from the group consisting of halogen, nitro, cyano, thiocyanato and a radical of the formula $B^1-Y^1$, $B^1$ and $Y^1$ being as defined further below, and/or having substituents which, in pairs, can form a spiro-linked ring selected from the $(C_3-C_7)$cycloalkyl group which is unsubstituted or substituted by one or more radicals selected from the group consisting of halogen, $(C_1-C_4)$alkyl, $(C_1-C_4)$haloalkyl and oxo, $R^2$ and $R^3$ independently of one another are hydrogen, amino, formyl, $(C_1-C_4)$alkyl, cyano$(C_1-C_4)$alkyl, $(C_1-C_4)$alkylamino, di$[(C_1-C_4)$alkyl]-amino, halo ($C_1$–$C_4$)alkyl, hydroxy($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_2$–$C_6$)alkenyl, halo($C_2$–$C_6$)alkenyl, ($C_2$–$C_6$)alkynyl, halo-($C_2$–$C_6$)alkynyl, ($C_1$–$C_4$)alkylamino-($C_1$–$C_4$)alkyl, di[($C_1$–$C_4$)alkyl]-amino-($C_1$–$C_4$)alkyl, ($C_3$–$C_9$) cycloalkylamino-($C_1$–$C_4$)alkyl, ($C_3$–$C_9$)cycloalkyl, ($C_3$–$C_9$)heterocyclyl-($C_1$–$C_4$)alkyl, the cyclic groups in the last-mentioned 3 radicals being unsubstituted or substituted by one or more radicals, preferably up to three radicals, selected from the group consisting of ($C_1$–$C_4$) alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, aminocarbonyl, ($C_1$–$C_4$)alkylaminocarbonyl, phenoxy-$C_1$–$C_4$)alkyl, phenyl-($C_1$–$C_4$)alkyl, heterocyclyl, heterocyclylamino, heterocyclyloxy, heterocyclylthio, or one of the last-mentioned 17 radicals which is substituted in the acyclic moiety or, preferably, in the cyclic moiety by one or more radicals selected from the group consisting of halogen, nitro, cyano, ($C_1$–$C_4$)alkyl, ($C_1$–$C_4$) alkoxy, ($C_1$–$C_4$)alkylthio, ($C_1$–$C_4$)haloalkyl, ($C_1$–$C_4$) haloalkoxy, formyl, ($C_1$–$C_4$)alkylcarbonyl, ($C_1$–$C_4$) alkoxycarbonyl and ($C_1$–$C_4$)alkoxy, heterocyclyl in the radicals in each case containing 3 to 9 ring atoms and 1 to 3 hetero ring atoms selected from the group consisting of N, O and S, or $R^2$ and $R^3$ together with the nitrogen atom of the group $NR^2R^3$ are a heterocyclic radical having 3 to 6 ring atoms and 1 to 2 hetero ring atoms, where, besides the nitrogen atom, the optional further hetero ring atom is selected from the group consisting of N, O and S and the radical is unsubstituted or substituted by one or more radicals selected from the group consisting of halogen, ($C_1$–$C_4$) alkyl and oxo, $R^4$ is hydrogen, amino, formyl, ($C_1$–$C_4$)alkyl, cyano-($C_1$–$C_4$)alkyl, ($C_1$–$C_4$)alkylamino, di[($C_1$–$C_4$)alkyl] amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$) alkylamino-($C_1$–$C_4$)alkyl, di[($C_1$–$C_4$)alkyl]amino-($C_1$–$C_4$)alkyl, ($C_3$–$C_9$)cycloalkylamino-($C_1$–$C_4$)alkyl, ($C_3$–$C_9$)cycloalkyl, ($C_3$–$C_9$)heterocyclyl-($C_1$–$C_4$)alkyl having 3 to 9 ring members, the cyclic groups in the last-mentioned 3 radicals being unsubstituted or substituted by one or more, preferably up to three, radicals selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$) alkoxycarbonyl-($C_1$–$C_4$)alkyl, ($C_1$–$C_4$) alkylaminocarbonyl-($C_1$–$C_4$)alkyl, ($C_1$–$C_4$) alkylcarbonyl, ($C_1$–$C_4$)alkoxycarbonyl, aminocarbonyl, ($C_1$–$C_4$)alkylaminocarbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the last-mentioned 17 radicals which is substituted in the acyclic moiety or, preferably, in the cyclic moiety by one or more radicals selected from the group consisting of halogen, nitro, cyano, ($C_1$–$C_4$)alkyl, ($C_1$–$C_4$)alkoxy, ($C_1$–$C_4$) alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl, ($C_1$–$C_4$) alkoxy, where heterocyclyl in the radicals contains in each case 3 to 9 ring atoms and 1 to 3 hetero ring atoms selected from the group consisting of N, O and S, $R^5$ is hydrogen, ($C_1$–$C_4$)alkyl, ($C_1$–$C_4$)haloalkyl or ($C_3$–$C_7$) cycloalkyl, A-Z is a divalent bridge of the formula —$CH_2CH_2$—,    —$CH_2CH_2CH_2$—,
—$CH_2CH_2CH_2CH_2$—,
—S—$CH_2$S—,  —S—$CH_2$—O—,  —O—$CH_2$—O—,
—S—$CH_2CH_2$S—,    —S—$CH_2CH_2$—O—,
—O—$CH_2CH_2$—O—,
—$CH_2CH_2CH_2$—NR—,  —$CH_2CH_2CH_2$—O—,
—$CH_2CH_2CH_2$—S—,
—S—CH=CH—S—,    O—CH=CH—O—,
—O—CH=CH—S—,
—CH=CH—$CH_2$—O—,  —CH=CH—$CH_2$—S,
—$CH_2CH_2$NR—,
—O—CH=N—,
—S—CH=N—,
—NR—CH=N,
—CH=CH—N=N—,
—N=CH—CH=N—,
—CH=CH—$CH_2$—,
—CH=CH—CH=CH— or
—CH=CH—NR—, where R in the groups NR is in each case H or methyl, (X')$_m$ denotes m substituents X' where the X' in each case independently of one another are halogen, ($C_1$–$C_4$)alkyl, ($C_2$–$C_4$)alkenyl, ($C_2$–$C_4$)alkynyl, ($C_1$–$C_4$)alkoxy, ($C_2$–$C_4$)alkenyloxy, ($C_2$–$C_4$)alkynyloxy, [($C_1$–$C_4$)alkyl] carbonyl, [($C_1$–$C_4$)alkoxy]carbonyl or [($C_1$–$C_4$) alkylthio]-carbonyl, the hydrocarbon-containing moieties in the last-mentioned 9 radicals being unsubstituted or substituted by one or more radicals selected from the halogen group, or are the oxo group, (X)$_n$ denotes n substituents X where the X in each case independently of one another are halogen, hydroxyl, amino, nitro, formyl, carboxyl, cyano, thiocyanato, ($C_1$–$C_4$)alkyl, cyano($C_1$–$C_4$)alkyl, ($C_1$–$C_4$)alkoxy, ($C_1$–$C_4$)alkylamino, di[($C_1$–$C_4$)alkyl]amino, halo($C_1$–$C_4$) alkyl, hydroxy-($C_1$–$C_4$)alkyl, ($C_1$–$C_4$)alkoxy-($C_1$–$C_4$) alkyl, halo($C_1$–$C_4$)alkoxy-($C_1$–$C_4$)alkyl, ($C_1$–$C_4$) alkylthio, halo($C_1$–$C_4$)alkylthio, ($C_2$–$C_6$)alkenyl, halo ($C_2$–$C_6$)alkenyl, ($C_2$–$C_6$)alkynyl, halo($C_2$–$C_6$)alkynyl, ($C_1$–$C_4$)alkylamino-($C_1$–$C_4$)alkyl, di[($C_1$–$C_4$)alkyl] amino-($C_1$–$C_4$)alkyl, ($C_3$–$C_9$)cycloalkylamino-($C_1$–$C_4$) alkyl, ($C_3$–$C_9$)cycloalkyl, heterocyclyl-($C_1$–$C_4$)alkyl having 3 to 9 ring members, the cyclic groups in the last-mentioned 3 radicals being unsubstituted or substituted by one or more radicals, preferably up to three radicals, selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, aminocarbonyl, ($C_1$–$C_4$)alkylaminocarbonyl, phenoxy-($C_1$–$C_4$)alkyl, phenyl-($C_1$–$C_4$)alkyl, heterocyclyl, heterocyclylamino, heterocyclyloxy, heterocyclylthio or one of the last-mentioned 17 radicals which is substituted in the acyclic moiety or, preferably, in the cyclic moiety by one or more radicals selected from the group consisting of halogen, nitro, cyano, ($C_1$–$C_4$)alkyl, ($C_1$–$C_4$) alkoxy, ($C_1$–$C_4$)alkylthio, ($C_1$–$C_4$)haloalkyl, ($C_1$–$C_4$) haloalkoxy, formyl, ($C_1$–$C_4$)alkylcarbonyl, ($C_1$–$C_4$) alkoxycarbonyl and ($C_1$–$C_4$)alkoxy, where heterocyclyl in the radicals contains in each case 3 to 9 ring atoms and 1 to 3 hetero ring atoms selected from the group consisting of N, O and S, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$alkyl and oxo, $B^1$ is a direct bond or a divalent group of the formula —O—, —S—, —CO—, —O—CO—, —CO—O—, —NR'—, —NR'—CO— or —CO—NR'—, where R' is H or $(C_1-C_4)$alkyl, $Y^1$ is H or an acyclic hydrocarbon radical having 1 to 4 carbon atoms, a cyclic hydrocarbon radical having 3 to 6 carbon atoms or a heterocyclic radical having 3 to 6 ring atoms and 1 to 3 hetero ring atoms selected from the group consisting of N, O and S, where each of the three last-mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, hydroxyl, amino, mono- and dialkylamino, $[(C_1-C_4)$alkoxy]carbonyl, $[(C_1-C_4)$alkyl]carbonyl, formyl, carbamoyl, mono- and di$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl.

Compounds of the formula (I) according to the invention and their salts which are furthermore of special interest are those in which $R^1$ is $(C_1-C_4)$alkyl, $(C_1-C_4)$haloalkyl, benzyl, $[(C_3-C_6)$cycloalkyl]-$(C_1-C_2)$-alkyl, $(C_3-C_6)$cycloalkyl or a heterocyclic radical having 3 to 6 ring atoms and 1 or 2 hetero ring atoms selected from the group consisting of N and O, preferably an oxygen atom as hetero ring atom, the cycloalkyl radical or the heterocyclic radical being in each case unsubstituted or substituted by one or more radicals selected from the group consisting of halogen, nitro, cyano, thiocyanato and a radical of the formula $B^1$—$Y^1$, where $B^1$ and $Y^1$ are as defined further below, and/or having substituents which, in pairs, can form a spiro-linked ring selected from the $(C_3-C_7)$cycloalkyl group which is unsubstituted or substituted by one or more radicals selected from the group consisting of halogen, $(C_1-C_4)$alkyl, $(C_1-C_4)$haloalkyl and oxo, $R^2$ and $R^3$ independently of one another are hydrogen, amino, formyl, $(C_1-C_4)$alkyl, $(C_1-C_4)$alkoxy-$(C_1-C_4)$alkyl, $(C_3-C_6)$alkenyl, $(C_3-C_6)$alkynyl, $(C_1-C_4)$alkylamino-$(C_1-C_4)$alkyl, di$[(C_1-C_4)$alkyl]-amino-$(C_1-C_4)$alkyl or phenyl, phenyl-$(C_1-C_4)$alkyl, phenylcarbonyl or phenoxycarbonyl or one of the last-mentioned four radicals which is up to trisubstituted in the phenyl moiety by radicals selected from the group consisting of halogen, $(C_1-C_4)$alkyl, $(C_1-C_4)$alkoxy and $(C_1-C_4)$alkoxycarbonyl, or $R^2$ and $R^3$ together with the nitrogen atom of the group $NR^2R^3$ are a heterocyclic radical having 3 to 6 ring atoms and 1 to 2 hetero ring atoms, where, besides the nitrogen atom, the optional further hetero ring atom is selected from the group consisting of N and O and the radical is unsubstituted or substituted by one or more radicals selected from the group consisting of halogen, $(C_1-C_4)$alkyl and oxo, $R^4$ is hydrogen, amino, formyl, $(C_1-C_4)$alkyl, di$[(C_1-C_4)$alkyl]amino, $(C_1-C_4)$alkoxy-$(C_1-C_4)$alkyl, $(C_3-C_6)$alkenyl, $(C_3-C_6)$alkynyl, $(C_1-C_4)$dialkylamino-$(C_1-C_4)$alkyl, phenyl, phenoxy-$(C_1-C_4)$alkyl, phenyl-$(C_1-C_4)$alkyl, phenoxycarbonyl, phenylaminocarbonyl or one of the last-mentioned five radicals which is monosubstituted to trisubstituted in the phenyl moiety by radicals selected from the group consisting of halogen, $(C_1-C_4)$alkyl, $(C_1-C_4)$alkoxy and $(C_1-C_4)$alkoxycarbonyl, $R^5$ is hydrogen, $(C_1-C_4)$alkyl, $(C_1-C_4)$haloalkyl or $(C_3-C_7)$cycloalkyl, A-Z is a divalent bridge of the formula
—$CH_2CH_2$—, —$CH_2CH_2CH_2$—,
—$CH_2CH_2CH_2CH_2$—,
—S—$CH_2CH_2$S—, —S—$CH_2CH_2$—O—,
—O—$CH_2CH_2$—O—,
—$CH_2CH_2CH_2$—NR—, —$CH_2CH_2CH_2$—O—,
—$CH_2CH_2CH_2$—S—,
—S—CH=CH—S—, O—CH=CH—O—,
—CH=CH—$CH_2$—O—, —O—CH=CH—S,
—$CH_2CH_2$NR—,
—O—CH=N—,
—S—CH=N—,
—NR—CH=N—,
—CH=CH—N=N—,
—N=CH—CH=N—,
—CH=CH—$CH_2$—,
—CH=CH—CH=CH— or
—CH=CH—NR, where R in the groups NR is in each case H or methyl, $(X')_m$ denotes m substituents X' where the X' in each case independently of one another are halogen, $(C_1-C_4)$alkyl or $(C_1-C_4)$alkoxy, $(X)_n$ denotes n substituents X where the X in each case independently of one another are halogen, hydroxyl, $(C_1-C_4)$alkyl or $(C_1-C_4)$alkoxy, $B^1$ is a direct bond or a divalent group of the formula —O—, —S— or —O—CO—, $Y^1$ is H, $(C_1-C_4)$alkyl, $(C_3-C_6)$cycloalkyl or phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, mono- and dialkylamino.

Preferred compounds of the formula (I) according to the invention and salts thereof are those in which $R^1$ is $(C_1-C_4)$alkyl, $(C_1-C_4)$haloalkyl or $[(C_3-C_6)$cycloalkyl]methyl, preferably —$CH_3$, —$CH_2F$, —$CHF_2$, —$CF_3$, —$CH_2Cl$, —$CHCl_2$, —$CCl_3$, —$CH_2Br$, —$CHBr_2$, —$CH_2CH_3$, —$CH_2CH_2F$, —$CF_2CHF_2$, —$CH_2CH_2Cl$, —$CH_2CH_2Br$, —$CH(CH_3)_2$, —$CF(CH_3)_2$, —$C(CH_3)_2Cl$ or cyclopropylmethyl, $R^2$ and $R^3$ independently of one another are hydrogen, formyl or $(C_1-C_4)$alkyl or $R^2$ and $R^3$ together with the nitrogen atom of the group $NR^2R^3$ are a heterocyclic radical having 4 to 6 ring atoms and 1 to 2 hetero ring atoms, where, besides the nitrogen atom, the optional further hetero ring atom is selected from the group consisting of N and O, $R^4$ is hydrogen or $(C_1-C_4)$alkyl, $R^5$ is H, $(C_1-C_4)$alkyl or $(C_1-C_4)$haloalkyl, preferably H, $CH_3$, $C_2H_5$, n- or i-$C_3H_7$, n-butyl or $CF_3$, in particular $CH_3$ or $C_2H_5$, A-Z is a divalent bridge of the formula
—$CH_2CH_2$—, —$CH_2CH_2CH_2$—,
—$CH_2CH_2CH_2CH_2$—,
—S—$CH_2CH_2$S, —O—$CH_2CH_2$—O—,
—$CH_2CH_2CH_2$—NR—, —$CH_2CH_2CH_2$—O—,
—$CH_2CH_2CH_2$—S—,
—$CH_2CH_2$NR—,
—N=CH—O—, —N=CH—S—, —N=CH—NR, —N=CH—CH=N—,
—CH=CH—CH$_2$—,
—CH=CH—CH=CH— or
—CH=CH—NR, where R in the groups NR is in each case H or methyl, preferably H.

(X')$_m$ denotes m substituents X' where the X' in each case independently of one another are halogen or (C$_1$–C$_4$)alkyl, and (X)$_n$ denotes n substituents X where the X in each case independently of one another are halogen, hydroxyl, (C$_1$–C$_4$)alkyl or (C$_1$–C$_4$)alkoxy.

Also preferred compounds of the formula (I) according to the invention and salts thereof are those which contain one or more of the characteristics of the abovementioned preferred compounds.

The present invention also relates to processes for the preparation of the compounds of the formula (I) or salts thereof, which comprises a) reacting a compound of the formula (II), $$R^1\text{-Fu} \quad (II)$$

where Fu is a functional group selected from the group consisting of carboxylic ester, carboxylic orthoester, carboxylic acid chloride, carboxamide, carboxylic anhydride and trichloromethyl, with a biguanidide of the formula (III) or an acid addition salt thereof

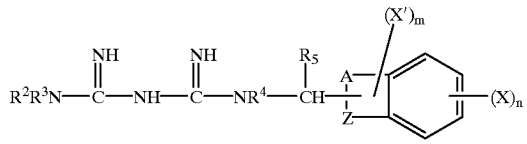
(III)

b) reacting a compound of the formula (IV)

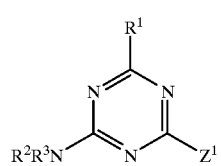
(IV)

where Z$^1$ is an exchangeable radical or a leaving group, for example chlorine, trichloromethyl, (C$_1$–C$_4$)alkylsulfonyl and unsubstituted or substituted phenyl-(C$_1$–C$_4$) alkylsulfonyl or (C$_1$–C$_4$)alkylphenyl-sulfonyl with a suitable amine of the formula (V) or an acid addition salt hereof

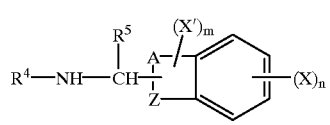
(V)

the radicals R$^1$, R$^2$, R$^3$, R$^4$, R$^5$, A, X', X, m and n in formulae (II), (Ill), (IV) and (V) being as defined in formula (I).

The reaction of the compounds of the formula (II) and (III) is preferably carried out with base catalysis in an inert organic solvent, for example tetrahydrofuran (THF), dioxane, acetonitrile, dimethylformamide (DMF), methanol and ethanol, at temperatures between –10° C. and the boiling point of the solvent, preferably at 20° C. to 60° C.; if acid addition salts of the formula (III) are used, they are liberated, as a rule, in situ with the aid of a base. Bases or basic catalysts which are suitable are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicylco[5.4.0]undec-7-ene (DBU). The base in question is employed for example in a range of from 0.1 to 3 mol equivalents based on the compound of the formula (III). For example, the compound of the formula (II) can be employed in equimolar amounts or up to an excess of 2 mol equivalents relative to the compound of the formula (III). In principle, the processes in question are known from the literature (cf.: Comprehensive Heterocyclic Chemistry, A. R. Katritzky, C. W. Rees, Pergamon Press, Oxford, New York, 1984, Vol.3; Part 2B; ISBN 0-08-030703-5, p.290).

The reaction of the compounds of the formula (IV) and (V) is preferably carried out with base catalysis in an inert organic solvent, for example THF, dioxane, acetonitrile, DMF, methanol and ethanol, at temperatures between –10° C. and the boiling point of the solvent or solvent mixture in question, preferably at 20° C. to 60° C., the compound (V), if employed in the form of the acid addition salt, optionally being liberated in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8diazabicylco[5.4.0]undec-7-ene (DBU). The base in question is employed, as a rule, in the range of from 1 to 3 mol equivalents based on the compound of the formula (IV), for example, the compound of the formula (IV) can be employed in equimolar amounts with the compound of the formula (V), or in an excess of up to 2 mol equivalents. In principle, the processes in question are known from the literature (cf. Comprehensive Heterocyclic Chemistry, A. R. Katritzky, C. W. Rees, Pergamon Press, Oxford, New York, 1984, Vol.3; Part 2B; ISBN 0-08-030703-5, p. 482).

The starting materials of the formulae (II), (III), (IV) and (V) are either commercially available or can be prepared by, or analogously to, processes known from the literature. For example, the compounds can also be prepared by one of the processes described hereinbelow.

The compound of the formula (IV), or a direct precursor thereof, may be prepared for example as follows:

1. By reacting a compound of the formula (II) with an amidinothiourea derivative of the formula (VI)

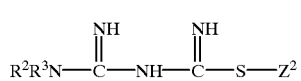
(VI)

where Z$^2$ is (C$_1$–C$_4$)alkyl or phenyl-(C$_1$–C$_4$)alkyl and R$^2$ and R$^3$ are as defined in formula (I), compounds of the formula (IV) are obtained in which Z$^1$=—SZ$^2$.

2. By reacting an amidine of the formula (VII) or an acid addition salt thereof

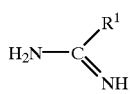

where $R^1$ is as defined in formula (I)
with an N-cyanodithioiminocarbonate of the formula (VIII)

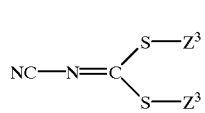

where $Z^3$ is ($C_1$–$C_4$)alkyl or phenyl($C_1$–$C_4$)alkyl, compounds of the formula (IV) are obtained where $Z^1$=—S—$Z^3$.

3. By reacting an alkali metal dicyanoamide with a carboxylic acid derivative of the abovementioned formula (II), compounds of the formula (IV) are obtained where $Z^1$=$NH_2$.

4. By reacting trichloroacetonitrile with a nitrile of the formula (IX)

where $R^1$ is as defined in formula (I), compounds of the formula (X)

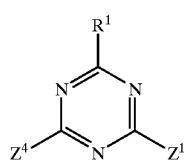

are first obtained where $Z^1$ and $Z^4$ are in each case $CCl_3$ and which lead to compounds of the formula (IV) where $Z^1$=$CCl_3$ by a subsequent reaction with compounds of the formula $HNR^2R^3$ ($R^2$ and $R^3$ as in formula (I)).

The reaction of the carboxylic acid derivatives of the formula (II) with the amidinothiourea derivatives of the formula (VI) is preferably carried out with base catalysis in an organic solvent, for example acetone, THF, dioxane, acetonitrile, DMF, methanol or ethanol at temperatures from –10° C. to the boiling point of the solvent, preferably at 0° C. to 20° C. However, the reaction can also be carried out in water or in aqueous solvent mixtures with one or more of the abovementioned organic solvents. If (VI) is employed as the acid addition salt, it may be liberated in situ with a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates, or organic bases such as triethylamine or 1,8-diazabicyclo[5.4.0]undec-7-ene (DBU). The base in question is employed, for example, in a range of from 1 to 3 mol equivalents based on the compound of the formula (VI). Compounds of the formula (II) and (VI) can be employed, for example, in equimolar amounts or in an excess of up to 2 mol equivalents of the compound of the formula (II). In principle, the processes in question are known from the literature (cf.: H. Eilingsfeld, H. Scheuermann, Chem. Ber.; 1967, 100,1874).

The reaction of the amidines of the formula (VII) with the N-cyanodithioiminocarbonates of the formula (VIII) is preferably carried out with base catalysis in an inert organic solvent, for example acetonitrile, DMF, dimethylacetamide (DMA), N-methylpyrrolidone (NMP), methanol and ethanol, at temperatures from –10° C. to the boiling point of the solvent, preferably at 20° C. to 80° C. If (VII) is employed as the acid addition salt, it can be liberated in situ using a base, if appropriate. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates, or organic bases such as triethylamine or 1,8-diazabicyclo[5.4.0]undec-7-ene (DBU). The base in question is employed, for example, in a range of from 1 to 3 mol equivalents based on the compound of the formula (VIII). Compounds of the formula (VII) and (VIII) can be employed, as a rule, in equimolar amounts or in an excess of up to 2 mol equivalents of the compound of the formula (II). In principle, the processes in question are known from the literature (cf.: T. A. Riley, W. J. Henney, N. K. Dalley, B. E. Wilson, R. K. Robins; J. Heterocyclic Chem.; 1986, 23 (6), 1706–1714).

The intermediates of the formula (X) where $Z^1$=chlorine can be prepared by reacting alkali metal dicyanamide with a carboxylic acid derivative of the formula (II), in which case Fu is preferably the functional group carboxylic acid chloride or carboxamide. The reactants are reacted, for example, with acid catalysis in an inert organic solvent, for example toluene, chlorobenzene or chlorinated hydrocarbons, at temperatures between –10° C. and the boiling point of the solvent, preferably at 20° C. to 80° C., it being possible for the intermediates formed to be chlorinated in situ with a suitable chlorinating reagent, such as, for example, phosphorus oxychloride. Examples of suitable acids are hydrohalic acids such as HCl, or else Lewis acids, for example $AlCl_3$ or $BF_3$ (cf. U.S. Pat. No. 5,095,113, DuPont).

Intermediates of the formula (X) where $Z^1$, $Z^4$=trihalomethyl can be prepared by reacting the corresponding trihaloacetonitriles with a carbonitrile of the formula (IX). The reactants are reacted, for example, with acid catalysis in an inert organic solvent, for example toluene, chlorobenzene or chlorinated hydrocarbons, at temperatures between –40° C. and the boiling point of the solvent, preferably at –10° C. to 30° C. Examples of suitable acids are hydrohalic acids, such as HCl, or else Lewis acids, for example $AlCl_3$ or $BF_3$ (cf. EP-A-1 30939, Ciba Geigy).

Intermediates of the formula (IV) where $Z^1$=($C_1$–$C_4$) alkylmercapto or unsubstituted phenyl-($C_1$–$C_4$)-alkylmercapto can be reacted in an inert organic solvent, for example toluene, chlorobenzene, chlorinated hydrocarbons or others, at temperatures between –40° C. and the boiling point of the solvent, preferably at 20° C. to 80° C., with a suitable chlorinating reagent, for example elemental chlorine or phosporus oxychloride to give more reactive chlorotriazines of the formula (IV) where $Z^1$=Cl (cf. J. K. Chakrabarti, D. E. Tupper; Tetrahedron 1975, 31(16), 1879–1882).

Intermediates of the formula (IV) where $Z^1$=($C_1$–$C_4$) alkylmercapto or unsubstituted or substituted phenyl-($C_1$–$C_4$)alkylmercapto or ($C_1$–$C_4$)alkyl-phenylthio can be oxidized in a suitable solvent, for example chlorinated hydrocarbons, acetic acid, water, alcohols, acetone or mixtures of these, at temperatures between 0° C. and the boiling point of the solvent, preferably from 20° C. to 80° C., using a suitable oxidant, for example m-chloroperbenzoic acid, hydrogen peroxide or potassium peroxomonosulfate (cf.: T. A. Riley, W. J. Henney, N. K. Dailey, B. E. Wilson, R. K. Robins; J. Heterocyclic Chem.; 1986, 23 (6), 1706–1714).

The biguanidides of the formula (III) can be prepared by reacting cyanoguanidines of the formula (XI)

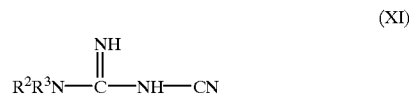
(XI)

where $R^2$ and $R^3$ are as defined in formula (I) with amines of the abovementioned formula (V), preferably in the form of the hydrohalides or other acid addition salts; the amines are also employed for preparing compounds (I) when using the alternative process b).

The reaction of the compounds (III) and (V) is carried out, as a rule, by reacting the compound (III) with the hydrochloride of the amine of the formula (V) in the presence of an inert organic, preferably higher-boiling, solvent at temperatures from 50° C. to the boiling point of the solvent, in particular 60 to 1 50° C. Suitable solvents are the organic solvents which have already been mentioned, for example THF or dichlorobenzene.

Processes which are suitable for the preparation of intermediates of the formula (V)

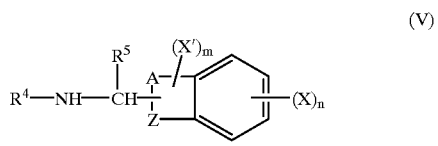
(V)

are those where compounds of the formula (XII)

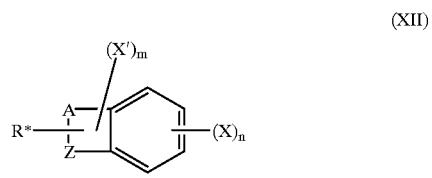
(XII)

in which A, X, X', Z, m and n are as defined in formula (V) and

1; in which R is a group of the formula

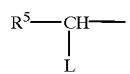

where L is a leaving group, for example halogen, such as chlorine, bromine or iodine, or the mesyl group, are reacted with ammonia or an amine $R^4$—$NH_2$, or 2. in which $R^*$ is a group of the formula $R^5$—CO—
are subjected to reductive amination with ammonia in the presence of a hydrogen source, for example a reducing agent such as Raney nickel, and, in the event that $R^4$ is other than hydrogen, the product is subjected to a suitable derivatization, 3. in which $R^*$ is a group of the formula $R^5$—C(=NOH)—
are reduced with hydrogen in the presence of a catalyst and the resulting compound (V) is subjected to a suitable derivatization, in the event that $R^4$ is other than hydrogen, where, in the formulae of variants 1 to 3, $R^5$ is in each case as defined in formula (V).

A process which is suitable, for example, for preparing intermediates of the formula (V) and their acid addition salts is one where ketones of the formula (XIII)

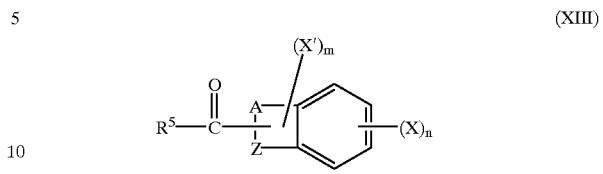
(XIII)

in which $R^5$, A, X, X', Z, m and n are as defined in formula (V) are either directly subjected to a reductive amination in accordance with the abovementioned variant 2, or first reacted with hydroxylamine hydrochloride under standard conditions, e.g. in aqueous alcoholic solution in the presence of a base, to give the corresponding oxime which is then reduced in accordance with the abovementioned variant 3 to give the compound of the formula V, $R^4$=H. If required, the product is derivatized to give other compounds $R^4$=H.

The reactions of variants 1 to 3 are known in principle and described in EP-0492615 analogously by way of example of preparing phenoxyalkylamines. The reaction conditions selected therein can, as a rule, also be applied when preparing compounds (V) from compounds of the formula (XIII). The ketones of the formula (XIII) are known from the literature (cf. JACS 97, 347 (1975); Bull. Soc. Chim. Fr. 1973 (Pt.2), 1285; Gazz. Chim. Ital. 107, 271 (1977); Heterocycles 26, 645 (1987)) or can be prepared analogously to processes known from the literature.

Acids which are suitable for preparing the acid addition salts of the compounds of the formula (I) are the following: hydrohalic acids, such as hydrochloric acid or hydrobromic acid, furthermore phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition compounds of the formula (I) can be prepared in a simple manner by customary salt formation methods, e.g. by dissolving a compound of the formula (I) in a suitable organic solvent, for example methanol, acetone, methylene chloride or petroleum ether, and adding the acid at temperatures from 0 to 100° C., and they may be isolated in a known manner, for example by filtration, and, if appropriate, purified by washing with an inert organic solvent.

The base addition salts of the compounds of the formula (I) are preferably prepared in inert polar solvents, for example water, methanol or acetone, at temperatures from 0 to 100° C. Examples of bases which are suitable for the preparation of the salts according to the invention are, for example, alkali metal carbonates, such as potassium carbonate, alkali metal hydroxides and alkaline earth metal hydroxides, e.g. NaOH or KOH, alkali metal hydrides and alkaline earth metal hydrides, e.g. NaH, alkali metal alkoxides and alkaline earth metal alkoxides, e.g. sodium methoxide, potassium tert-butoxide, or ammonia or ethanolamine. The "inert solvents" mentioned in the process variants above are to be understood as meaning in each case solvents which are inert under the reaction conditions in question, but which need not be inert under any reaction conditions. The compounds of the formula (I) according to the invention and the salts thereof, hereinbelow together termed compounds of the formula (I) (according to the invention), have an excellent herbicidal activity against a broad spectrum of economically important monocotyledonous and dicotyledonous harmful plants. The active substances also act efficiently on perennial weeds which produce shoots from rhizomes, rootstocks or other perennial organs and which are difficult to control. In this context, it does not matter whether the substances are applied pre-plant, pre-emergence or post-emergence.

Specifically, examples may be mentioned of some representatives of the monocotyledonous and dicotyledonous weed flora which can be controlled by the compounds according to the invention, without these being a restriction to certain species.

Examples of weed species on which the active substances act efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the spectrum of action extends to species such as Galium, Viola, Veronica, Lamium, Stellaria, Amaranthus, Sinapis, lpomoea, Matricaria, Abutilon and Sida from amongst the annuals, and Convolvulus, Cirsium, Rumex and Artemisia in the case of the perennial weeds.

The active substances according to the invention also effect outstanding control of weeds which occur under the specific conditions of rice growing, for example Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage, but then their growth stops and, eventually, after three to four weeks have elapsed, they die completely.

If the active substances are applied post-emergence to the green parts of the plants, growth equally stops drastically a very short time after the treatment, and the weed plants remain at the growth stage of the point of time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledonous weeds, crop plants of economically important crops, for example wheat, barley, rye, rice, maize, sugar beet, cotton and soya, are damaged not at all, or only to a negligible extent. For these reasons, the present compounds are highly suitable for selectively controlling undesirable vegetation in agricultural crops.

In addition, the substances according to the invention have outstanding growth-regulating properties in crop plants. They engage in the plant metabolism in a regulating manner and can thus be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be employed in the form of wettable powders, emulsifiable concentrates, sprayable solutions, dusts or granules in the customary preparations. The invention therefore also relates to herbicidal and plant growth-regulating compositions which comprise compounds of the formula (I).

The compounds of the formula (I) can be formulated in various ways, depending on the biological and/or chemico-physical parameters which prevail. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag Munich, 4th Edition 1986, Wade van Valkenburg, "Pesticide Formulations", Marcel Dekker, N.Y., 1973; K. Martens, "Spray Drying Handbook", 3rd Edition 1979, G. Goodwin Ltd. London.

The formulation auxiliaries required, such as inert materials, surfactants, solvents and other additives are also known and described, for example, in: Watkins, "Handbook of Insecticide Dust Diluents and Carriers", 2nd Edition, Darland Books, Caldwell N. J., H. v. Olphen, "Introduction to Clay Colloid Chemistry"; 2nd Edition, J. Wiley & Sons, N.Y.; C. Marsden, "Solvents Guide"; 2nd Edition, Interscience, N.Y. 1963; McCutcheon's "Detergents and Emulsifiers Annual", MC Publ. Corp., Ridgewood N. J.; Sisley and Wood, "Encyclopedia of Surface Active Agents", Chem. Publ. Co. Inc., N.Y. 1964; Schönfeldt, "Grenzfl ächenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Edition 1986.

Based on these formulations, it is also possible to prepare combinations with other pesticidally active substances, for example insecticides, acaricides, herbicides, fungicides, and also with safeners, fertilizers and/or growth regulators, for example in the form of a readymix or a tank mix.

Wettable powders are preparations which are uniformly dispersible in water and which, besides the active substance, also comprise ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalene-sulfonate, or else sodium oleoylmethyltaurinate, in addition to a diluent or inert substance. To prepare the wettable powders, the herbicidally active ingredients are ground finely, for example in customary apparatus such as hammer mills, blower mills and air-jet mills, and simultaneously or subsequently mixed with the formulation auxiliaries.

Emulsifiable concentrates are prepared by dissolving the active substance in an organic solvent, for example butanol, cyclohexanone, dimethylformamide, xylene, or else higher-boiling aromatics or hydrocarbons, or mixtures of the organic solvents with the addition of one or more ionic and/or nonionic surfactants (emulsifiers). Examples of substances which can be used as emulsifiers are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active substance with finely distributed solid substances, for example talc, natural clays such as kaolin, bentonite and pyrophyllite, or diatomaceous earth.

Suspension concentrates can be water- or oil-based. They can be prepared, for example, by wet grinding using commercially availiable bead mills with or without an addition of surfactants, for example those which have already been mentioned above in the case of the other formulation types.

Emulsions, for example oil-in-water emulsions (EW), can be prepared, for example, by means of stirrers, colloid mills and/or static mixers using aqueous organic solvents in the presence or absence of surfactants which have already been mentioned above, for example, in the case of the other formulation types.

Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers.

As a rule, water-dispersible granules are prepared by the customary processes such as spray drying, fluidized-bed granulation, disk granulation, mixing with high-speed mixers, and extrusion without solid inert material.

For the preparation of disk, fluidized-bed, extruder and spray granules see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation components. In the case of emulsifiable concentrates, the concentration of active substance may be approximately 1 to 90, preferably 5 to 80, % by weight. Formulations in the form of dusts comprise 1 to 30% by weight of active substance, in most cases preferably 5 to 20% by weight, of active substance; sprayable solutions comprise approximately 0.05 to 80, preferably 2 to 50, % by weight of active substance. In the case of water-dispersible granules, the active substance compound depends partly on whether the active compound is in liquid or solid form and on which granulation auxiliaries, fillers and the like are being used. The active substance content of the water-dispersible granules is, for example, between 1 and 95% by weight, preferably between 10 and 80% by weight.

Besides, the abovementioned formulations of active substances may comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active substances according to the invention in mixed formulations or in tank mixes are, for example, known active substances as they are described, for example, in Weed Research 26, 441–445 (1986), or "The Pesticide Manual", 10th edition, The British Crop Protection Council and the Royal Soc. of Chemistry, 1994, and the literature cited therein. Examples of active substances which may be mentioned as herbicides which are known from the literature and which can be combined with the compounds of the formula (I) are the following (note: either the common names in accordance with the International Organization for Standardization (ISO) or the chemical names, if appropriate together with a customary code number, of the compounds are given): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]-acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H. i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CEDC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (e.g. clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (e.g. butyl ester, DEH-1 12); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfon-amide; ethoxyfen and its esters (e.g. ethyl ester, HN-252); etobenzanid (HW 52); fenoprop; fenoxan, fenoxaprop and fenoxaprop-P and their esters, e.g. fenoxaprop-P-ethyl and fenoxaprop-ethyl; fenoxydim; fenuron; flamprop-methyl; flazasulfuron; fluazifop and fluazifop-P and their esters, e.g. fluazifop-butyl and fluazifop-P-butyl; fluchloralin; flumetsulam; flumeturon; flumiclorac and its esters (e.g. pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (e.g. methyl ester, NC-319); haloxyfop and its esters; haloxyfop-P (=R-haloxyfop) and its esters; hexazinone; imazamethabenzmethyl; imazapyr; imazaquin and salts, such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyidymron; metabenzuron; methobenzuron; methobromuron; metolachlor; metosulam (XRD 511); metoxuron; metribuzin; metsulfuronmethyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (e.g. propargyl ester); quinclorac; quinmerac; quinofop and its ester derivatives, quizalofop and quizalofop-P and their ester derivatives, e.g. quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]A4,5,6,7-tetrahydro-2H-indazole; secbumeton; sethoxydim; siduron; simazine; simetryn; SN 106279, i.e. 2-[[7-[2chloro-4-(trifluoromethyl)phenoxy]-2-naphthalenyl]oxy]-propanoic acid and its methyl ester; sulcotrione, sulfentrazone (FMC-97285, F6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thizopyr (Mon-13200); thidiazimin (SN-24085); thifensulfuron-methyl; thiobencarb; tiocarbazil; tralkoxydim; tri-allate; triasullfuron; triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)phenyl]-1H-tetrazole; UBH-509; D489; LS 82-556; KPP-300; NC-324; NC-330; KH-218; DPX-N8189; SC-0774; DOWCO-535; DK-8910; V-53482; PP600; MBH-001; KIH-9201; ET-751; KIH-6127 and KIH-2023.

For use, the formulations which are in commercially available form are, if desired, diluted in the customary manner, for example using water in the case of wettable powders, emulsifiable concentrates, dispersions and water-dispersible granules. Preparations in the form of dusts, soil granules, granules for broadcasting and sprayable solutions are usually not diluted any further with other inert substances prior to use.

The necessary rate of application of the compounds of the formula (I) varies with the external conditions such as, inter alia, temperature, humidity and the nature of the herbicide used. It may vary within wide limits, for example between 0.001 and 10.0 kg/ha or more of active ingredient, but it is preferably between 0.005 and 5 kg/ha.

A. CHEMICAL EXAMPLES

Example A1

2-Amino-4-(1-fluoro-1-methylethyl)-6-[1-(indan-2-yl)-1-ethylamino]-1,3,5-triazine (see Table 2, Example 2.17)

A methoxide solution prepared from 1.2 g (0.05 mol) of sodium and 100 ml of methanol is added to 7.0 g (0.025 mol) of 1-biguanidino-1-(indan-2-yl)ethane hydrochloride in 50 ml of methanol and 7 g of ground molecular sieve 3 Å. Then, 6.0 g (0.045 mol) of ethyl 1-fluoroisobutyrate are added, and the mixture is stirred for 2 hours at 25° C. and then for 4 hours at 65° C. The reaction mixture is filtered, the filtrate is concentrated, and the residue is taken up in ethyl acetate. The mixture is washed with water, and the organic phase is separated off and dried with sodium sulfate. The desiccant is filtered off and the solvent is evaporated in vacuo. After purification by column chromatography (eluent: ethyl acetate), 4.8 g (61% of theory) of 2-amino-4-(1-fluoro-1-methylethyl)6-[1-(indan-2-yl)-1-ethylamino]-1,3,5-triazine are obtained.

Example A2

2-Amino-4-isopropyl-6-[1-(1-methylbenzimidazol-2-yl)-1-ethylamino]-1,3,5-triazine (see Table 16, Example 16.3)

2.6 g (0.015 mol) of 2-amino-4-chloro-6-isopropyl-1,3,5-triazine and 4.2 g (0.03 mol) of $K_2CO_3$ are introduced into 50 ml of acetonitrile. 3.8 g (0.015 mol) of 1-methylbenzimidazole hydrobromide are added to this solution, and the mixture is subsequently refluxed for 3 hours. Then, all solid constituents are filtered off with suction and the filtrate is evaporated on a rotary evaporator. The residue is purified by means of column chromatography (eluent: ethyl acetate). This gives 4.1 g (88% of theory) of 2-amino-4-isopropyl-6-[1-(1-methylbenzimidazol-2-yl)-1-ethylamino]-1,3,5-triazine.

The compounds described in Tables 1 to 17 are obtained by, or analogously to, the above Examples A1 and A2. The abbreviations in the table denote:

| | |
|---|---|
| No. | = Example or Example number |
| Phys. Data | = Characteristic physical data of the compound |
| Me | = methyl |
| OMe | = methoxy |
| Et | = ethyl |
| Pr | = propyl |
| i-Pr | = isopropyl |
| c-Pr | = cyclopropyl |
| 1-Me-c-Pr | = 1-methylcyclopropyl |
| c-$C_5H_9$ | = cyclopentyl |
| c-$C_4H_7$ | = cyclobutyl |
| c-$C_6H_{11}$ | = cyclohexyl |
| t-Bu | = tertiary butyl |
| Ph | = phenyl |
| $(X)_n$ | = position and nature of the substituent on the phenyl ring (position 1 = bond to A); "—" = no substituent on the phenyl ring (n = O) |

TABLE 1

Compounds of the formula (Ia)

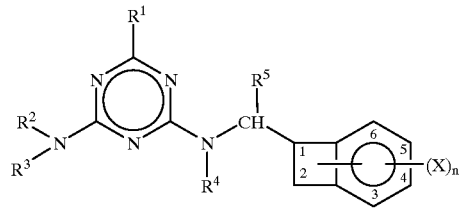

(Ia)

| No. | R¹ | R² | R³ | R⁴ | R⁵ | (X)$_n$ | Phys. Data |
|---|---|---|---|---|---|---|---|
| 1.1 | CF₃ | H | H | H | Me | — | |
| 1.2 | CF₂CHF₂ | H | H | H | Me | 5-Me | |
| 1.3 | i-Pr | H | H | H | Me | — | |
| 1.4 | i-Pr | H | H | H | Et | — | |
| 1.5 | i-Pr | H | H | H | Me | 5-Me | |
| 1.6 | CF(CH₃)₂ | H | H | H | Me | — | |
| 1.7 | CF(CH₃)₂ | H | H | H | Et | — | |
| 1.8 | CF(CH₃)₂ | H | H | H | Me | 4,5-Me₂ | |
| 1.9 | c-C₅H₉ | H | H | H | Me | — | |
| 1.10 | c-Pr | H | H | H | Me | — | |
| 1.11 | CF(CH₃)₂ | CHO | H | H | Me | — | |
| 1.12 | CF(CH₃)₂ | CHO | Me | H | Me | — | |
| 1.13 | CF(CH₃)₂ | COMe | H | H | Me | — | |
| 1.14 | CF(CH₃)₂ | COMe | Me | H | Me | — | |
| 1.15 | CF₃ | COPh | H | H | Me | — | |
| 1.16 | CF₃ | COOPh | H | H | Me | — | |
| 1.17 | CF(CH₃)₂ | —(CH₂)₅— | | H | Me | — | |
| 1.18 | CF(CH₃)₂ | —(CH₂)₂—O—(CH₂)₂— | | H | Me | — | |

TABLE 2

Compounds of the formula (Ib)

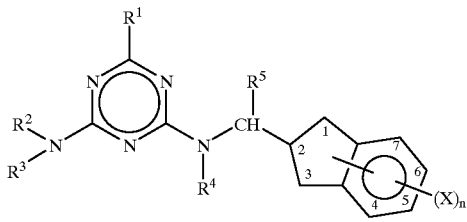

(Ib)

| No. | R¹ | R² | R³ | R⁴ | R⁵ | (X)$_n$ | Phys. Data |
|---|---|---|---|---|---|---|---|
| 2.1 | CF₃ | H | H | H | Et | — | |
| 2.2 | CF₃ | H | H | H | Me | — | |
| 2.3 | CF₂CHF₂ | H | H | H | Me | — | |
| 2.4 | CF₂CHF₂ | H | H | H | Et | — | |
| 2.5 | CCl(CH₃)₂ | H | H | H | Me | — | |
| 2.6 | CCl(CH₃)₂ | H | H | H | Et | — | |
| 2.7 | CBr(CH₃)₂ | H | H | H | Me | — | |
| 2.8 | CBr(CH₃)₂ | H | H | H | Me | 5-Me | |
| 2.9 | CBr(CH₃)₂ | H | H | H | Et | 5-Me | |
| 2.10 | i-Pr | H | H | H | Me | — | NMR, see end of table |
| 2.11 | i-Pr | Me | Me | H | Me | — | |
| 2.12 | i-Pr | H | H | Me | Me | — | |
| 2.13 | i-Pr | Me | H | H | Me | — | |
| 2.14 | i-Pr | H | H | H | Me | 5-Me | |
| 2.15 | i-Pr | H | H | H | Me | 5,6-Me₂ | NMR, see end of table |
| 2.16 | CF(CH₃)₂ | H | H | H | Me | 4-Cl | |
| 2.17 | CF(CH₃)₂ | H | H | H | Me | — | NMR, see end |

TABLE 2-continued

Compounds of the formula (Ib)

(Ib)

| No. | R$^1$ | R$^2$ | R$^3$ | R$^4$ | R$^5$ | (X)$_n$ | Phys. Data |
|---|---|---|---|---|---|---|---|
| | | | | | | | of table |
| 2.18 | CF(CH$_3$)$_2$ | H | H | H | Et | — | |
| 2.19 | CF(CH$_3$)$_2$ | H | H | H | Pr | — | |
| 2.20 | CF(CH$_3$)$_2$ | H | H | H | Me | 5-Me | |
| 2.21 | CF(CH$_3$)$_2$ | H | H | H | Me | 5,6-Me$_2$ | |
| 2.22 | CF(CH$_3$)$_2$ | H | H | H | Me | 5-OCH$_3$ | |
| 2.23 | CF(CH$_3$)$_2$ | H | H | H | CF$_3$ | — | |
| 2.24 | CHF$_2$ | H | H | H | Me | — | |
| 2.25 | C$_6$H$_5$—CH$_2$ | H | H | H | Me | — | |
| 2.26 | t-Bu | H | H | H | Me | — | |
| 2.27 | CH$_2$CH(CH$_3$)$_2$ | H | H | H | Me | — | |
| 2.28 | CH$_2$CH$_2$OCH$_3$ | H | H | H | Me | — | |
| 2.29 | CH(OCH$_3$)CH$_3$ | H | H | H | Me | — | |
| 2.30 | c-Pr | H | H | H | Me | — | |
| 2.31 | 1-Me-c-Pr | H | H | H | Me | — | |
| 2.32 | 1-F-Pr | H | H | H | Me | — | |
| 2.33 | (epoxide with CH$_3$) | H | H | H | Me | — | |
| 2.34 | c-Pr-CH$_2$ | H | H | H | Me | — | |
| 2.35 | c-Pr-CH$_2$ | H | H | H | Et | — | |
| 2.36 | CF(CH$_3$)$_2$ | CHO | H | H | Me | — | |
| 2.37 | c-Pr-CH$_2$ | COMe | H | H | Me | — | |
| 2.38 | c-Pr-CH$_2$ | COPh | H | H | Me | — | |
| 2.39 | c-Pr-CH$_2$ | Et | Et | H | Me | — | |
| 2.40 | CF(CH$_3$)$_2$ | H | H | H | c-Pr | — | |
| 2.41 | CF(CH$_3$)$_2$ | H | H | H | c-C$_5$H$_9$ | — | |
| 2.42 | CH(CH$_3$)$_2$ | H | H | H | c-Pr | — | |
| 2.43 | CH(CH$_3$)$_2$ | H | H | H | c-C$_5$H$_9$ | — | |
| 2.44 | CF(CH$_3$)$_2$ | H | H | H | i-Pr | — | |
| 2.45 | CH(CH$_3$)$_2$ | H | H | H | i-Pr | — | |
| 2.46 | CH(CH$_3$)$_2$ | H | H | H | CHMeEt | — | |
| 2.47 | CF(CH$_3$)$_2$ | H | H | H | CHMeEt | — | |
| 2.48 | CH(CH$_3$)$_2$ | H | H | H | CH$_2$F | — | |
| 2.49 | CF(CH$_3$)$_2$ | H | H | H | CH$_2$F | — | |
| 2.50 | CH(CH$_3$)$_2$ | H | H | H | CHMeOMe | — | |
| 2.51 | CF(CH$_3$)$_2$ | H | H | H | CHMeOMe | — | |
| 2.52 | CF(CH$_3$)$_2$ | H | H | H | t-Bu | — | |
| 2.53 | CH(CH$_3$)$_2$ | H | H | H | t-Bu | — | |
| 2.54 | c-Pr | H | H | H | c-Pr | — | |
| 2.55 | c-Pr | H | H | H | 2-Me-c-Pr | — | |
| 2.56 | CH(CH$_3$)$_2$ | H | H | H | Et | 5,6-Cl$_2$ | |
| 2.57 | COH(CH$_3$)$_2$ | H | H | H | Me | — | |
| 2.58 | nC$_3$H$_7$ | H | H | H | Et | — | |
| 2.59 | Ph | H | H | H | Me | — | |
| 2.60 | CH$_2$CF$_3$ | H | H | H | Me | — | |
| 2.61 | CH$_2$CF$_3$ | H | H | H | Me | — | |
| 2.62 | CH$_2$CF$_3$ | H | H | H | Et | — | |
| 2.63 | CH$_2$CF$_3$ | H | H | H | c-Pr | — | |
| 2.64 | CF(CH$_3$)$_2$ | H | H | H | CF$_2$CF$_3$ | — | |
| 2.65 | CF(CH$_3$)$_2$ | H | H | H | CH$_2$CF$_3$ | — | |
| 2.66 | CF(CH$_3$)$_2$ | H | H | H | CCl$_3$ | — | |
| 2.67 | i-Pr | H | H | H | CCl$_3$ | — | |
| 2.68 | i-Pr | H | H | H | CH$_2$CF$_3$ | — | |
| 2.89 | CF(CH$_3$)$_2$ | H | H | H | Me | 4-Me | |
| 2.70 | i-Pr | H | H | H | Et | — | |
| 2.71 | CH$_2$CH(CH$_3$)$_2$ | H | H | H | Me | 5-Me | |

TABLE 2-continued

Compounds of the formula (Ib)

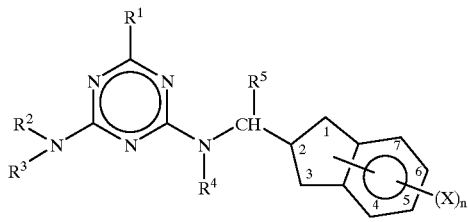

(Ib)

| No. | R¹ | R² | R³ | R⁴ | R⁵ | (X)$_n$ | Phys. Data |
|---|---|---|---|---|---|---|---|
| 2.72 | CH$_2$CH(CH$_3$)$_2$ | H | H | H | Me | — | |
| 2.73 | CHCH$_3$C$_2$H$_5$ | H | H | H | Me | — | |
| 2.74 | CHCH$_3$OCH$_3$ | H | H | H | H | — | |

NMR data of individual examples:

Example 2.10

$^1$H NMR (CDCl$_3$): δ=1.2 (m, 9H); 2.6 (m, 1 H); 2.8 (m, 2H); 3.0 (m, 2H); 4.2 (m, 1H); 7.1 (m, 4H)

Example 2.15

$^1$H NMR (CDCl$_3$): δ=1.2 (m, 9H); 2.2 (s, 6H); 2.5 (m, 1H); 2.7 (m, 2H); 2.9(m, 2H); 4.2 (m, 1H); 7.0 (s, 1 H); 7.0 (s, 1 H)

Example 2.17

$^1$H NMR (DMSO-$_6$): δ=1.1 (d, 3H); 1.5 (s, 3H); 1.6 (s, 3H); 2.7 (m, 2H); 2.9 (m, 2H); 4.1 (m, 1H); 7.1 (m, 4H)

TABLE 3

Compounds of the formula (Ic)

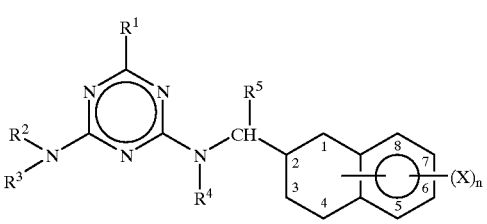

(Ic)

| No. | R¹ | R² | R³ | R⁴ | R⁵ | (X)$_n$ | Phys. Data |
|---|---|---|---|---|---|---|---|
| 3.1 | Me | H | H | H | Me | — | |
| 3.2 | Et | H | H | H | Me | — | |
| 3.3 | Et | H | H | H | Et | — | |
| 3.4 | Pr | H | H | H | Pr | — | |
| 3.5 | t-Bu | H | H | H | Me | — | |
| 3.6 | t-Bu | H | H | H | Et | — | |
| 3.7 | t-Bu | H | H | Me | Me | — | |
| 3.8 | i-Pr | H | H | H | Me | — | |
| 3.9 | i-Pr | H | H | H | Et | — | |
| 3.10 | CF(CH$_3$)$_2$ | H | H | H | Me | — | |
| 3.11 | CF(CH$_3$)$_2$ | H | H | H | Et | — | |
| 3.12 | CF(CH$_3$)$_2$ | H | H | H | Me | 6,7-Me$_2$ | |
| 3.13 | 1-Cl-c-Pr | H | H | H | Et | — | |
| 3.14 | CF(CH$_3$)$_2$ | H | H | H | CF$_3$ | — | |
| 3.15 | CH(CH$_3$)$_2$ | H | H | H | CF$_3$ | — | |
| 3.16 | CF(CH$_3$)$_2$ | Me | Me | H | CF$_2$CHF$_2$ | — | |
| 3.17 | CF(CH$_3$)$_2$ | CHO | H | H | Me | — | |
| 3.18 | CF(CH$_3$)$_2$ | CHO | Me | Me | Me | — | |
| 3.19 | c-Pr-CH$_2$ | H | H | H | Me | — | |
| 3.20 | c-Pr-CH$_2$ | Me | Me | H | Me | — | |
| 3.21 | CF(CH$_3$)$_2$ | H | H | Me | Me | — | |
| 3.22 | CF(CH$_3$)$_2$ | H | H | H | c-Pr | — | |
| 3.23 | CH(CH$_3$)$_2$ | H | H | H | c-Pr | — | |
| 3.24 | CF(CH$_3$)$_2$ | H | H | H | i-Pr | — | |
| 3.25 | CH(CH$_3$)$_2$ | H | H | H | i-Pr | — | |
| 3.26 | CF(CH$_3$)$_2$ | H | H | H | c-Pr | 5-OMe | |
| 3.27 | CH(CH$_3$)$_2$ | H | H | H | c-Pr | 5-OMe | |
| 3.28 | CF(CH$_3$)$_2$ | H | H | H | c-Pr | 5-Cl | |
| 3.29 | CH(CH$_3$)$_2$ | H | H | H | c-Pr | 5-Cl | |
| 3.30 | CF(CH$_3$)$_2$ | H | H | H | t-Bu | — | |
| 3.31 | CH(CH$_3$)$_2$ | H | H | H | t-Bu | — | |
| 3.32 | c-Pr | H | H | H | Me | — | |
| 3.33 | c-Pr | H | H | H | Et | — | |
| 3.34 | c-Pr | H | H | H | c-Pr | — | |
| 3.35 | CF(CH$_3$)$_2$ | H | H | H | CF$_3$ | — | |
| 3.36 | CH(CH$_3$)$_2$ | H | H | H | CF$_3$ | — | |
| 3.37 | CF(CH$_3$)$_2$ | H | H | H | CH$_2$F | — | |

TABLE 4

Compounds of the formula (Ie)

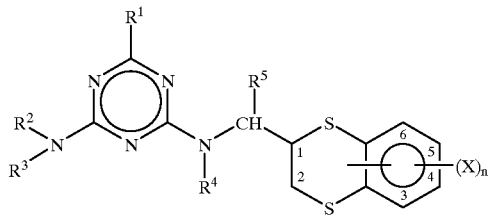

(Ie)

| No. | $R^1$ | $R^2$ | $R^3$ | $R^4$ | $R^5$ | $(X)_n$ | Phys. Data |
|---|---|---|---|---|---|---|---|
| 4.1 | i-Pr | H | H | H | Me | — | |
| 4.2 | i-Pr | H | H | H | Et | — | |
| 4.3 | i-Pr | H | H | H | i-Pr | 3,6-F$_2$ | |
| 4.4 | i-Pr | H | H | H | Me | 4,5-F$_2$ | |
| 4.5 | Me | H | H | Pr | Me | — | |
| 4.6 | Me | Et | Et | H | Me | — | |
| 4.7 | CHF$_2$ | Me | Me | H | H | — | |
| 4.8 | CHF$_2$ | Me | Et | H | H | — | |
| 4.9 | 1-OH-c-Pr | H | H | H | Et | — | |

TABLE 4-continued

Compounds of the formula (Ie)

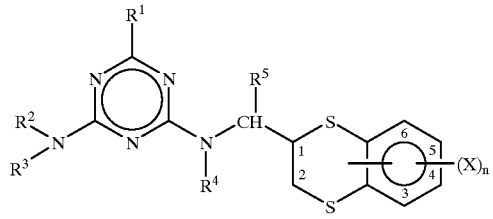

(Ie)

| No. | $R^1$ | $R^2$ | $R^3$ | $R^4$ | $R^5$ | $(X)_n$ | Phys. Data |
|---|---|---|---|---|---|---|---|
| 4.10 | | H | H | H | Me | — | |
| 4.11 | CF(CH$_3$)$_2$ | CHO | H | H | Me | — | |
| 4.12 | CF(CH$_3$)$_2$ | H | H | CHO | Me | — | |
| 4.13 | CF$_3$(CH$_3$)$_2$ | COMe | H | H | Me | — | |
| 4.14 | c-Pr-CH$_2$ | H | H | H | Me | — | |
| 4.15 | c-Pr-CH$_2$ | H | H | H | Et | — | |
| 4.16 | CF(CH$_3$)$_2$ | COOMe | H | H | Me | — | |
| 4.17 | CF$_3$ | H | H | H | Me | — | |

TABLE 5

Compounds of the formula (If)

(If)

| No. | $R^1$ | $R^2$ | $R^3$ | $R^4$ | $R^5$ | $(X)_n$ | Phys. Data |
|---|---|---|---|---|---|---|---|
| 5.1 | i-Pr | H | H | H | H | 3,6-(OCH$_3$)$_2$ | |
| 5.2 | i-Pr | H | H | H | H | 2-Me | |
| 5.3 | Et | H | H | CH$_3$ | H | — | |
| 5.4 | Et | H | H | H | Me | — | |
| 5.5 | CH$_2$CH$_2$CH$_2$Cl | H | H | H | Et | — | |
| 5.6 | CHCl$_2$ | H | H | H | Et | — | |
| 5.7 | CH$_2$CH$_2$OCH$_3$ | H | H | H | Et | — | |
| 5.8 | CF(CH$_3$)$_2$ | H | H | H | Me | — | |
| 5.9 | CF$_3$ | H | H | H | Me | 6-COMe | |
| 5.10 | CF$_3$ | H | H | H | Me | — | |
| 5.11 | CF(CH$_3$)$_2$ | Me | H | H | Me | — | |
| 5.12 | CF(CH$_3$)$_2$ | CHO | H | H | Me | — | |
| 5.13 | c-Pr-CH$_2$ | H | H | H | Me | — | |
| 5.14 | c-Pr-CH$_2$ | H | H | H | Et | — | |
| 5.15 | CF$_3$ | —(CH$_2$)$_4$— | | H | Me | | |
| 5.16 | CF$_3$ | (CH$_2$)$_2$—O—(CH$_2$)$_2$ | | H | Me | | |

TABLE 6

Compounds of the formula (Ig)

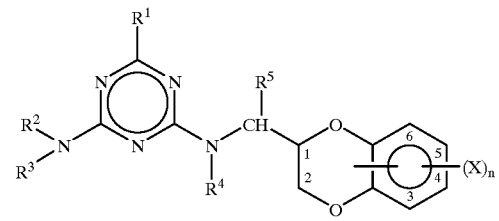

(Ig)

| No. | R¹ | R² | R³ | R⁴ | R⁵ | (X)$_n$ | Phys. Data |
|---|---|---|---|---|---|---|---|
| 6.1 | i-Pr | H | H | H | Me | — | |
| 6.2 | i-Pr | H | H | H | Me | 5-Me | NMR, see end of table |
| 6.3 | i-Pr | H | H | H | Et | — | |
| 6.4 | i-Pr | H | H | H | Et | 5-Me | |
| 6.5 | i-Pr | H | H | H | Me | 4,5-Cl$_2$ | |
| 6.6 | i-Pr | H | H | H | Me | 3,6-Br$_2$ | |
| 6.7 | CF(CH$_3$)$_2$ | H | H | H | Me | — | NMR, see end of table |
| 6.8 | CF(CH$_3$)$_2$ | H | H | H | Et | — | |
| 6.9 | CF(CH$_3$)$_2$ | H | H | H | Me | 5-Me | NMR, see end of table |
| 6.10 | CF(CH$_3$)$_2$ | H | H | H | Me | — | |
| 6.11 | CF$_2$CHF$_2$ | H | H | H | Et | 4,5-F$_2$ | |
| 6.12 | c-Pr | H | H | H | Me | — | |
| 6.13 | 1-F-c-Pr | H | H | H | Me | — | |
| 6.14 | 1-OMe-c-Pr | H | H | H | Me | — | |
| 6.15 | CH$_2$CH(CH$_3$)$_2$ | H | H | H | Me | — | |
| 6.16 | CCl(CH$_3$)$_2$ | H | H | H | Me | — | |

NMR data of some examples:

Example 6.2

$^1$H NMR (CDCl$_3$): δ=1.2 (m, 9H); 2.2 (s, 3H); 3.94.3 (m, 4H); 6.7 (m, 3H)

Example 6.7

$^1$H NMR (DMSO-d$_6$): δ=1.2 (m, 3H); 1.5 (s, 3H); 1.6 (s, 3H);
3.9–4.3 (m, 4H); 6.8 (m, 4H)

Example 6.9

$^1$H NMR (CDCl$_3$): δ=1.3 (m, 3H); 1.6 (s, 3H); 1.7 (s, 3H); 2.2 (s, 3H); 3.9–4.3 (m, 4H); 6.7 (m, 3H)

TABLE 7

Compounds of the formula (Ih)

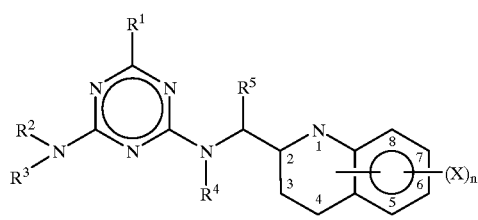

(Ih)

| No. | R¹ | R² | R³ | R⁴ | R⁵ | (X)$_n$ | Phys. Data |
|---|---|---|---|---|---|---|---|
| 7.1 | CH$_2$CH$_2$F | Me | H | H | Me | 1-Me | |
| 7.2 | CH$_2$CH$_2$Br | CHO | H | H | Me | 1,6-Me$_2$ | |

TABLE 7-continued

Compounds of the formula (Ih)

| No. | R¹ | R² | R³ | R⁴ | R⁵ | (X)$_n$ | Phys. Data |
|---|---|---|---|---|---|---|---|
| 7.3 | i-Pr | H | H | H | i-Pr | 1-Me | |
| 7.4 | i-Pr | CHO | H | H | i-Pr | 1-Et | |
| 7.5 | 1-Me-c-Pr | H | H | H | Me | — | |
| 7.6 | CF(CH$_3$)$_2$ | H | H | H | Me | — | |
| 7.7 | CF(CH$_3$)$_2$ | Me | Me | H | Me | — | |
| 7.8 | CF(CH$_3$)$_2$ | Et | Et | H | Me | — | |

TABLE 8

Compounds of the formula (Ij)

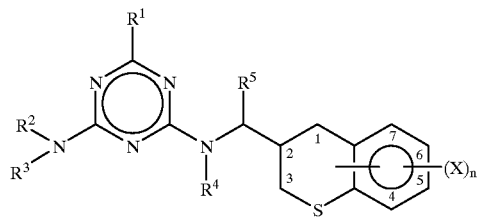

(Ij)

| No. | R¹ | R² | R³ | R⁴ | R⁵ | (X)$_n$ | Phys. Data |
|---|---|---|---|---|---|---|---|
| 8.1 | i-Pr | H | H | H | Me | — | |
| 8.2 | i-Pr | H | H | Me | Me | — | |
| 8.3 | i-Pr | H | H | Et | Me | — | |
| 8.4 | i-Pr | H | H | H | Et | 3-Me | |
| 8.5 | CF(CH$_3$)$_2$ | H | H | H | Me | — | |
| 8.6 | CH$_2$F | Me | Me | H | H | — | |
| 8.7 | CF$_3$ | Et | Et | H | H | — | |

TABLE 9

Compounds of the formula (Ik)

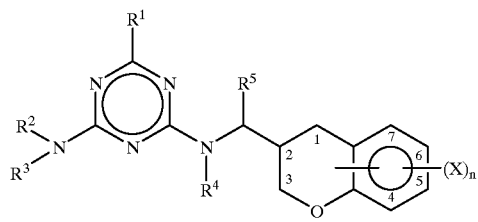

(Ik)

| No. | R¹ | R² | R³ | R⁴ | R⁵ | (X)$_n$ | Phys. Data |
|---|---|---|---|---|---|---|---|
| 9.1 | CF(CH$_3$)$_2$ | H | H | H | CH$_3$ | — | |
| 9.2 | CF(CH$_3$)$_2$ | H | H | H | Et | — | |
| 9.3 | t-Bu | H | H | H | Me | — | |
| 9.4 | n-C$_4$H$_9$ | H | H | H | Et | — | |
| 9.5 | CH$_2$CH(CH$_3$)$_2$ | H | H | H | Et | — | |
| 9.6 | i-Pr | H | H | H | Me | 6-Me | |

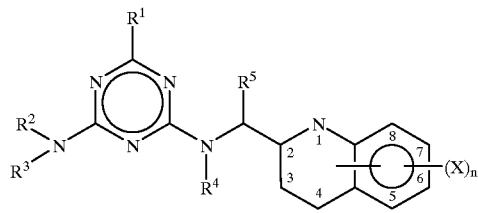

TABLE 9-continued

Compounds of the formula (Ik)

(Ik)

| No. | R$^1$ | R$^2$ | R$^3$ | R$^4$ | R$^5$ | (X)$_n$ | Phys. Data |
|---|---|---|---|---|---|---|---|
| 9.7 | i-Pr | H | H | H | Me | — | |
| 9.8 | i-Pr | H | H | H | Me | 6-Me | |
| 9.9 | i-Pr | H | H | H | Me | 6-Cl | |
| 9.10 | i-Pr | H | H | H | Me | 6-Br | |
| 9.11 | i-Pr | H | H | H | Me | 6-F | |
| 9.12 | i-Pr | H | H | H | Me | 4,6-Me$_2$ | |
| 9.13 | i-Pr | H | H | H | Me | — | |

TABLE 10

Compounds of the formula (IL)

(IL)

| No. | R$^1$ | R$^2$ | R$^3$ | R$^4$ | R$^5$ | (X)$_n$ | Phys. Data |
|---|---|---|---|---|---|---|---|
| 10.1 | CF(CH$_3$)$_2$ | H | H | H | Me | 4,6-Me$_2$ | |
| 10.2 | CF(CH$_3$)$_2$ | H | H | H | Me | — | |
| 10.3 | CF(CH$_3$)$_2$ | H | H | H | Me | 2-Me | |
| 10.4 | CF(CH$_3$)$_2$ | H | H | H | Me | 6-Me | |
| 10.5 | CF(CH$_3$)$_2$ | H | H | H | Et | — | |
| 10.6 | CF(CH$_3$)$_2$ | H | H | H | Et | 6-Me | |
| 10.7 | i-Pr | H | H | H | Me | 6-Me | |
| 10.8 | i-Pr | H | H | H | Me | — | |
| 10.9 | CF$_2$CHF$_2$ | H | H | H | Me | — | |
| 10.10 | CF$_2$CHF$_2$ | H | H | H | Me | 3-OCH$_3$ | |
| 10.11 | 1-F-c-Pr | H | H | H | Me | — | |
| 10.12 | i-Pr | H | H | H | Et | — | |
| 10.13 | i-Pr | H | H | H | Et | — | |
| 10.14 | CF(CH$_3$)$_2$ | H | H | H | Me | 6-OCH$_3$ | |
| 10.15 | CF(CH$_3$)$_2$ | H | H | H | Me | 6-Cl | |
| 10.16 | CH(CH$_3$)$_2$ | H | H | H | Me | 6-OCH$_3$ | |
| 10.17 | CH(CH$_3$)$_2$ | H | H | H | Me | 6-Cl | |
| 10.18 | CF(CH$_3$)$_2$ | H | H | H | i-Pr | — | |
| 10.19 | CH(CH$_3$)$_2$ | H | H | H | i-Pr | — | |
| 10.20 | CF(CH$_3$)$_2$ | H | H | H | c-Pr | — | |
| 10.21 | CH(CH$_3$)$_2$ | H | H | H | c-Pr | — | |
| 10.22 | CH(CH$_3$)$_2$ | H | H | H | CF$_3$ | — | |
| 10.23 | CF(CH$_3$)$_2$ | H | H | H | CF$_3$ | — | |
| 10.24 | CH(CH$_3$)$_2$ | H | H | H | CH$_2$F | — | |
| 10.25 | CF(CH$_3$)$_2$ | H | H | H | CH$_2$F | — | |
| 10.26 | CF(CH$_3$)$_2$ | H | H | H | Et | 6-Me | |
| 10.27 | CF(CH$_3$)$_2$ | H | H | H | Me | 6-Me | |
| 10.28 | CF(CH$_3$)$_2$ | H | H | H | n-Pr | — | |
| 10.29 | CH(CH$_3$)$_2$ | H | H | H | n-Pr | — | |
| 10.30 | CF(CH$_3$)$_2$ | H | H | H | CH$_2$CCl$_3$ | — | |
| 10.31 | CF(CH$_3$)$_2$ | H | H | H | CH$_2$CF$_3$ | — | |
| 10.32 | i-Pr | H | H | H | CF$_2$CF$_3$ | — | |
| 10.33 | CH$_2$—CH(CH$_3$)$_2$ | H | H | H | CF$_3$ | — | |

TABLE 10-continued

Compounds of the formula (IL)

(IL)

| No. | R$^1$ | R$^2$ | R$^3$ | R$^4$ | R$^5$ | (X)$_n$ | Phys. Data |
|---|---|---|---|---|---|---|---|
| 10.34 | CF(CH$_3$)$_2$ | H | H | H | c-C$_5$H$_9$ | — | |
| 10.35 | CH(CH$_3$)$_2$ | H | H | H | c-C$_4$H$_7$ | — | |
| 10.36 | CF(CH$_3$)$_2$ | H | H | H | c-C$_6$H$_{11}$ | — | |
| 10.37 | CF(CH$_3$)$_2$ | H | H | H | t-Bu | — | |
| 10.38 | CH(CH$_3$)$_2$ | H | H | H | t-Bu | — | |

TABLE 11

Compounds of the formula (Im)

(Im)

| No. | R$^1$ | R$^2$ | R$^3$ | R$^4$ | R$^5$ | (X)$_n$ | Phys. Data |
|---|---|---|---|---|---|---|---|
| 11.1 | t-Bu | CH$_3$ | H | H | Me | — | |
| 11.2 | t-Bu | CH$_3$ | H | Me | i-Pr | — | |
| 11.3 | t-Bu | CH$_3$ | H | H | H | — | |
| 11.4 | t-Bu | CH$_3$ | H | H | Me | — | |
| 11.5 | CH$_3$ | H | H | H | Me | — | |
| 11.6 | CH$_3$ | H | H | H | Et | — | |
| 11.7 | i-Pr | H | H | H | Me | — | |
| 11.8 | i-Pr | H | H | H | Me | 5-Cl | |
| 11.9 | CF(CH$_3$)$_2$ | H | H | H | CH$_3$ | — | |
| 11.10 | CF(CH$_3$)$_2$ | Me | Me | H | CH$_3$ | — | |
| 11.11 | CF(CH$_3$)$_2$ | Pr | H | H | CH$_3$ | — | |

TABLE 12

Compounds of the formula (In)

(In)

| No. | R$^1$ | R$^2$ | R$^3$ | R$^4$ | R$^5$ | (X)$_n$ | Phys. Data |
|---|---|---|---|---|---|---|---|
| 12.1 | CF$_3$ | H | H | H | Me | — | |
| 12.2 | CF$_3$ | H | H | H | Et | 5,6-Me$_2$ | |
| 12.3 | CCl$_3$ | H | H | H | Me | — | |

TABLE 12-continued

Compounds of the formula (In)

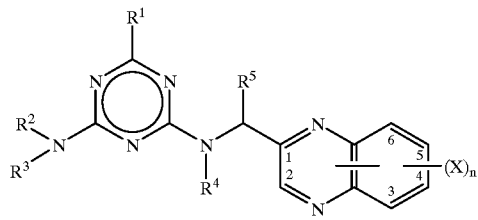

(In)

| No. | R¹ | R² | R³ | R⁴ | R⁵ | (X)ₙ | Phys. Data |
|---|---|---|---|---|---|---|---|
| 12.4 | CCl3 | H | H | H | Et | — | |
| 12.5 | t-Bu | H | H | Me | Me | — | |
| 12.6 | t-Bu | Me | Me | H | H | — | |
| 12.7 | i-Pr | H | H | H | Me | — | |
| 12.8 | i-Pr | H | H | H | Et | — | |
| 12.9 | i-Pr | H | H | H | Pr | — | |
| 12.10 | $CF(CH_3)_2$ | H | H | H | Me | 5,6-Me₂ | |
| 12.11 | $CF(CH_3)_2$ | H | H | Me | — | | |
| 12.12 | $CF(CH_3)_2$ | H | H | H | Et | — | |

TABLE 13

Compounds of the formula (Io)

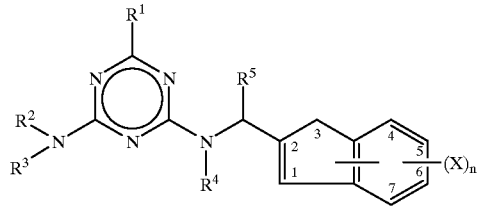

(Io)

| No. | R¹ | R² | R³ | R⁴ | R⁵ | (X)ₙ | Phys. Data |
|---|---|---|---|---|---|---|---|
| 13.1 | $CHOCH_3CH_3$ | H | H | H | Me | — | |
| 13.2 | $CHOCH_3CH_3$ | H | H | H | Et | — | |
| 13.3 | i-Pr | H | H | H | i-Pr | — | |
| 13.4 | i-Pr | H | H | Me | i-Pr | — | |
| 13.5 | $CF_2CF_3$ | H | H | H | Me | — | |
| 13.6 | $CF_2CF_3$ | H | H | H | Et | — | |
| 13.7 | $CH_2CH(CH_3)_2$ | H | H | H | Me | — | |

TABLE 14

Compounds of the formula (Ip)

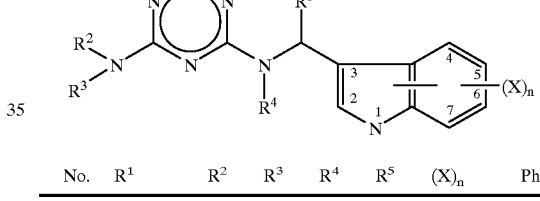

(Ip)

| No. | R¹ | R² | R³ | R⁴ | R⁵ | (X)ₙ | Phys. Data |
|---|---|---|---|---|---|---|---|
| 14.1 | $CH_2F$ | H | H | H | Me | — | |
| 14.2 | CCl₃ | H | H | H | Me | 6-OCH₃ | |
| 14.3 | CF₃ | H | H | H | Me | 6-OCH₃ | |

TABLE 14-continued

Compounds of the formula (Ip)

| No. | R¹ | R² | R³ | R⁴ | R⁵ | (X)ₙ | Phys. Data |
|---|---|---|---|---|---|---|---|
| 14.4 | i-Pr | H | H | H | Me | 6-Me | |
| 14.5 | i-Pr | H | H | H | Me | — | |
| 14.6 | i-Pr | H | H | H | Me | 6-OCH₃ | |
| 14.7 | $CF(CH_3)_2$ | H | H | H | Me | — | |
| 14.8 | $CF(CH_3)_2$ | H | H | H | Me | 7-CH₃ | |
| 14.9 | c-Pr | H | H | H | Me | — | |

TABLE 15

Compounds of the formula (Iq)

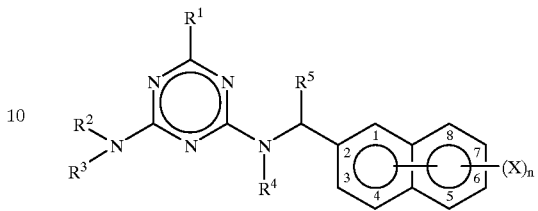

(Iq)

| No. | R¹ | R² | R³ | R⁴ | R⁵ | (X)ₙ | Phys. Data |
|---|---|---|---|---|---|---|---|
| 15.1 | c-Pr | H | H | H | Me | 1-Me | |
| 15.2 | CPr | H | H | H | Et | 1-Me | |
| 15.3 | CPr | H | H | H | Me | 1-Et | |
| 15.4 | c-C₅H₁₀ | H | H | H | Me | 1-Me | |
| 15.5 | $CF(CH_3)_2$ | H | H | H | Me | 1-Me | |

TABLE 16

Compounds of the formula (Ir)

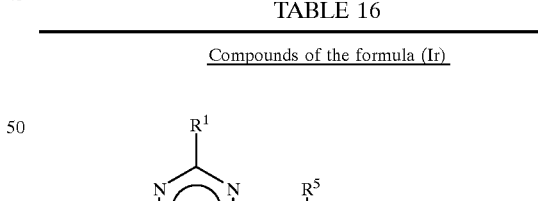

(Ir)

| No. | R¹ | R² | R³ | R⁴ | R⁵ | Y | (X)ₙ | Phys. Data |
|---|---|---|---|---|---|---|---|---|
| 16.1 | i-Pr | H | H | H | Me | O | 5-Me | NMR, see end of table |
| 16.2 | i-Pr | H | H | H | Me | S | — | NMR, see end of table |
| 16.3 | i-Pr | H | H | H | Me | NCH₃ | — | NMR, see end of table |
| 16.4 | i-Pr | H | H | H | Me | O | 4,6-Me₂ | NMR, see end of table |
| 16.5 | i-Pr | H | H | H | Me | S | 5-Me | NMR, see end |

TABLE 16-continued

Compounds of the formula (Ir)

(Ir)

| No. | R$^1$ | R$^2$ | R$^3$ | R$^4$ | R$^5$ | Y | (X)$_n$ | Phys. Data |
|---|---|---|---|---|---|---|---|---|
| 16.6 | i-Pr | H | H | H | Me | O | 6-t-Bu | NMR, see end of table |
| 16.7 | i-Pr | H | H | H | Me | O | 5,6-(CH$_2$)$_4$ | NMR, see end of table |

NMR data of some examples:

Example 16.1

$^1$H NMR (CDCl$_3$): δ=1.2 (d, 6H); 1.6 (d, 3H); 2.4 (s, 3H); 5.4 (m, 1H); 7.2 (d, 1H); 7.5 (s, 1H); 7.6 (d, 1H) 25

Example 16.2

$^1$H NMR (DMSO-d$_6$): δ=1.2 (d, 6H); 1.6 (d, 3H); 5.5 (m, 1H); 7.2 (m, 2H); 8.0 (m, 2H)

Example 16.3

$^1$H NMR (DMSO-d$_6$): δ=1.1 (d, 6H); 1.6 (d, 3H); 3.8 (s, 3H); 7.2 (m, 2H); 7.5 (m, 2H)

Example 16.4

$^1$H NMR (DMSO-d$_6$): δ=1.2 (d, 6H); 1.6 (d, 3H); 2.4 (s, 3H); 2.4 (s, 3H); 5.4 (m, 1H); 7.0 (s, 1H); 7.3 (s, 1H)

Example 16.5

$^1$H NMR (DMSO$_6$): δ=1.2 (d, 6H); 1.6 (d, 3H); 2.4 (s, 3H); 5.4 (m, 1H); 7.3 (d, $_1$H); 7.8 (m, 2H)

Example 16.6

$^1$H NMR (DMSO-$_6$): δ=1.2 (d, 6H); 1.3 (s, 9H); 1.6 (d, 3H); 5.4 (m, 1H); 7.4 (d, 1H); 7.7 (s, 1H); 7.8 (d, 1H)

Example 16.8

$^1$H NMR (CDCl$_3$): δ=1.2 (d, 6H); 1.6 (d, 3H); 5.1 (m, 1H); 7.2 (s, 1H); 7.4 (s, 1H)

TABLE 17

Compounds of the formula (Is)

(Is)

| No. | R$^1$ | R$^2$ | R$^3$ | R$^4$ | R$^5$ | (X)$_n$ | Phys. Data |
|---|---|---|---|---|---|---|---|
| 17.1 | CH$_3$ | H | H | H | Me | — | |
| 17.2 | i-Pr | H | H | H | Me | — | |
| 17.3 | i-Pr | H | H | H | Me | 6-Me | |
| 17.4 | CF$_2$CHF$_2$ | H | H | H | Et | — | |
| 17.5 | CCl(CH$_3$)$_2$ | H | H | H | Et | — | |

B. FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing parts by weight of a compound of the formula (I), 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of a compound of the formula (I) with 6 parts by weight of alkylphenyl polyglyckol ether (®Triton X 207), 3 parts by weight of isotridecanol polyglycol ether (8 EO) and 71 parts by weight of paraffinic mineral oil (boiling range, for example, approx. 255 to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Water-dispersible granules are obtained by mixing 75 parts by weight of a compound of the formula (I),
10" calcium lignosulfonate,
5" sodium lauryl sulfate,
3" polyvinyl alcohol and
7" kaolin grinding the mixture on a pinned-disk mill and granulating the powder in a fluidized bed by spraying on water as granulation liquid.

f) Water-dispersible granules are also obtained by homogenizing and precomminuting, on a colloid mill, 25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water, subsequently grinding the mixture on a bead mill and atomizing and drying the resulting suspension in a spray tower by means of a single-substance nozzle.

C. BIOLOGICAL EXAMPLES

1. Pre-emergence effect on weeds

Seeds or rhizome pieces of monocotyledonous and dicotyledonous weed plants were placed in sandy loam soil in plastic pots and covered with soil. The compounds according to the invention formulated as wettable powders or emulsion concentrates are then applied to the surface of the soil cover in the form of aqueous suspensions or emulsions at an application rate of 600 to 800 l of water/ha (converted), in various dosages.

After the treatment, the pots are placed in the greenhouse and kept under good growth conditions for the weeds. After the test plants have emerged after a test period of 3 to 4 weeks, the damage to the plants or the negative effect on emergence is scored visually by comparison with untreated controls. As shown by the test results, the compounds according to the invention have a good herbicidal pre-emergence activity against a broad spectrum of grass weeds and dicotyledonous weeds. For example, Examples No. 2.5, 2.10, 2.17, 2.18, 2.20, 2.30, 2.68, 2.70, 2.71, 2.72, 3.8, 3.10, 6.1, 6.7, 6.9, 6.16, 10.2, 10.8, 16.1 and 16.2 of Tables 2, 3, 6, 10 and 16 have a very good herbicidal activity in the test against harmful plants such as *Stellaria media, Lolium multiflorum, Matricaria inodora, Echinochloa crus-galli, Sinapis alba, Avena sativa, Cyperus esculentus* and *Cyperus iria* when applied pre-emergence at a rate of application of 1.25 kg or less of active substance per hectare.

2. Post-emergence effect on weeds

Seeds or rhizome pieces of monocotyledonous and dicotyledonous weeds are placed in sandy loam soil in plastic pots, covered with soil and grown in the greenhouse under good growth conditions. Three weeks after sowing, the test plants are treated in the three-leaf stage. The compounds according to the invention, formulated as wettable powders or as emulsion concentrates, are sprayed in various dosages onto the green parts of the plants at a rate of application of 600 to 800 l of water/ha (converted). After the test plants have remained in the greenhouse for approximately 3 to 4 weeks under optimal growth conditions, the effect of the preparations is scored visually by comparison with untrearted controls. The compositions according to the invention also have a good herbicidal activity against a broad spectrum of economically important grass weeds and dicotyledonous weeds when used post-emergence. For example, Examples No. 2.5, 2.10, 2.17, 2.18, 3.10, 6.1, 6.2, 6.7, 6.9, 16.1 and 16.2 of Tables 2, 3, 6 and 16 have a very good herbicidal activity in the test against harmful plants such as *Sinapis alba, Echinochloa crus-galli, Lolium multiflorum, Stellaria media, Matricaria inodora, Cyperus esculentus, Cyperus iria* and *Avena sativa* when applied post-emergence at a rate of application of 1.25 kg and less of active substance per hectare.

3. Effect on harmful plants in rice

Transplanted and sown rice as well as dicotyledonous weeds and grass weeds which typically occur in rice are grown in the greenhouse until they have reached the three-leaf stage (Echinochloa 1.5 leaves) under paddy rice conditions in closed plastic pots (flooding level of the water: 2–3 cm). They are then treated with the compounds according to the invention. To this end, the formulated active substances are suspended, dissolved or emulsified in water and applied in various dosages by pouring the suspensions, solutions or emulsions into the water with which the test plants are flooded. After the treatment has been carried out thus, the test plants are placed in the greenhouse under optimal growth conditions and maintained thus during the entire test period.

Approximately three weeks after application, the test is evaluated by scoring the damage to the plants visually in comparison with untreated controls. The compounds according to the invention have a very good herbicidal activity against harmful plants. For example, compounds of Examples 2.10, 2.17, 2.18, 2.20, 2.30, 2.68, 2.70, 2.71, 2.72, 3.10, 6.1, 6.7, 6.16, 10.2 and 10.8 of Tables 2, 3, 6 and 10 have, in the test, a very good activity against harmful plants which are typical of rice crops, for example *Cyperus monti, Echinochloa crus-galli* and *Sagittaria pygmaea*.

4. Crop plant tolerance

In further greenhouse experiments, seeds of a substantial number of crop plants and weeds are placed in sandy loam soil and covered with soil. Some of the pots are treated immediately as described in Section 1, while the remaining ones are placed in the greenhouse until the plants have developed two to three true leaves and are then sprayed with various dosages of the substances of the formula (I) according to the invention as described in Section 2. Visual scoring four to five weeks after the application and after the plants have remained in the greenhouse reveals that the compounds according to the invention do not damage dicotyledonous crops such as soybeans, cotton, oilseed rape, sugar beet and potatoes when used pre- and post-emergence, even when high dosages of active substance are used. Moreover, some substances also leave Gramineae crops such as barley, wheat, rye, Sorghum species, maize or rice unharmed. Some of the compounds of the formula (I) are highly selective and are therefore suitable for controlling undesirable plant growth in agricultural crops.

We claim:

1. A compound of the formula

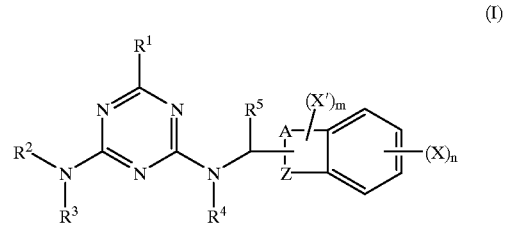

(I)

or a salt thereof, in which $R^1$ is $(C_1-C_6)$alkyl
which is unsubstituted or substituted by one or more radicals selected from the group consisting of halogen, cyano, nitro, thiocyanato, hydroxyl, $(C_1-C_4)$ alkoxy, $(C_1-C_4)$ alkylthio, $(C_1-C_4)$alkylsulfinyl, $(C_1-C_4)$ alkylsulfonyl, $(C_2-C_4)$ alkenyl, $(C_2-C_4)$alkynyl, phenyl which is unsubstituted or substituted by one or more radicals from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, amino, mono- and di[$(C_1-C_4)$alkyl]amino, $(C_1-C_4)$alkanoylamino, benzoylamino, nitro, cyano, [$(C_1-C_4)$alkoxy]carbonyl, [$(C_1-C_4)$alkyl]carbonyl, formyl, carbamoyl, mono- and di-[$(C_1-C_4)$alkyl]aminocarbonyl and $(C_1-C_4)$ alkylsulfonyl, and $(C_3-C_9)$cycloalkyl which is unsubstituted or substituted by one or more $(C_1-C_4)$alkyl radicals, and a heterocyclic ring having 3 to 6 ring atoms and one hetero atom selected from the group consisting of N, O and S, the heterocyclic ring being unsubstituted or substituted by one or more radicals selected from the group consisting of halogen, $(C_1-C_4)$ alkyl and oxo, and a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, the heterocyclic ring being unsubstituted or substituted by one or more radicals selected from the group consisting of halogen, $(C_1-C_4)$alkyl and oxo, or is $(C_3-C_7)$cycloalkyl, $(C_3-C_7)$cycloalkenyl or a heterocyclic ring having 3 to 6 ring atoms and one hetero atom selected from the group consisting of N, O and S, or a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, the cycloalkyl, cycloalkenyl or heterocyclic radical in each case being unsubstituted or substituted by one or more radicals selected from the group consisting of halogen, nitro, cyano, thiocyanato and a radical of the formula $B^1$—$Y^1$, where $B^1$ and $Y^1$ are as defined further below, wherein the pairs of substituents optionally form a fused benzene, or a fused or spirolinked ring selected from the group consisting of $(C_3-C_7)$cycloalkyl, $(C_3-C_7)$cycolalkenyl and a heterocyclic ring having 3 to 6 ring atoms and one hetero atom selected from the group consisting of N, O and S, the benzene, cycloalkyl, cycloalkenyl or heterocyclic ring being unsubstituted or substituted by one or more radicals selected from the group consisting of halogen, $(C_1-C_4)$alkyl, $(C_1-C_4)$haloalkyl and oxo, or is phenyl which is unsubstituted or substituted by one or more radicals selected from the group consisting of halogen $(C_1-C_4)$alkyl, $(C_1-C_4)$haloalkyl, $(C_1-C_4)$alkoxy, $(C_1-C_4)$haloalkoxy, $(C_1-C_4)$alkylthio, hydroxyl, amino, nitro, carboxy, cyano, azido, $[(C_1-C_4)$alkoxy]carbonyl, $[(C_1-C_4)$alkyl]carbonyl, formyl, carbamoyl, mono- and di$[(C_1-C_4)$alkyl]aminocarbonyl, mono- and di-$[(C_1-C_4)$alkyl]amino, $(C_1-C_4)$alkanoylamino, benzoylamino, $(C_1-C_4)$alkylsulfinyl, $(C_1-C_4)$haloalkylsulfinyl, $(C_1-C_4)$alkylsulfonyl and $(C_1-C_4)$haloalkylsulfonyl, $R^2$ and $R^3$ in each case independently of one another are hydrogen, amino or alkylamino or dialkylamino, each of which has 1 to 4 carbon atoms in the alkyl radical, an acyclic or cyclic hydrocarbon radical or hydrocarbon-oxy radical, each of which has 1 to 6 carbon atoms, or a heterocyclyl radical, heterocycyloxy radical or heterocyclylamino radical, each of which has 3 to 6 ring atoms and one hetero ring atom selected from the group consisting of N, O and S, where each of the five last-mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di$[(C_1-C_4)$alkyl] aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, or $R^2$ and $R^3$ together with the nitrogen atom of the group $NR^2R^3$ are a heterocyclic radical having 3 to 6 ring atoms and one hetero atom selected from the group consisting of N, O and S or are piperazinyl or morpholinyl, and the radical is unsubstituted or substituted by one or more radicals selected from the group consisting of halogen, $(C_1-C_4)$alkyl, $(C_1-C_4)$haloalkyl and oxo, $R^4$ is hydrogen, amino, alkylamino or dialkylamino, each of which has 1 to 6 carbon atoms in the alkyl radical, an acyclic or cyclic hydrocarbon radical or hydrocarbon-oxy radical having in each case 1 to 10 carbon atoms, or a heterocyclyl, heterocyclyloxy or heterocyclylamino, the heterocyclyl portion in each case is a heterocyclic radical heterocyclic ring having 3 to 6 ring atoms and one hetero atom selected from the group consisting of N, O and S, or is a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, each of the hydrocarbon, hydrocarbonoxy, heterocyclyl, heterocycloyloxy or heterocyclylamino radicals are unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and diakylamino, nitro, carboxyl, cyano, azido, $[(C_1-C_4)$alkoxy]carbonyl, $[(C_1-C_4)$alkyl]carbonyl, formyl, carbamoyl, mono- and di$[C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, $R^5$ is hydrogen, nitro, cyano, thiocyanato or a radical of the formula —$B^2$—$Y^2$, where $B^2$ and $Y^2$ are as defined further below, A-Z is a divalent bridge of the formula —$(CH_2)_a$—, where a is the integer 2, 3 or 4, —$W^1$—$(CH_2)_b$—$W^2$—, where b is the integer 1 or 2 and $W^1$, $W^2$ independently of one another are NR, O or S, —$CH_2CH_2CH_2$—$W^3$—, where $W^3$ is NR, O or S, —$W^4$—CH=CH—$W^5$—, where $W^4$, $W^5$ independently of one another are NR, O or S, —CH=CH—$CH_2$—$W^6$—, where $W^6$ is a group of the formula NR, O or S, or

—$CH_2CH_2NR$—,

—$W^7$—CH=N—, where $W^7$ is a group NR, O or S,

—$W^8CH_2$—N=N—, where $W^8$ is a group NR, O or S,

—CH=CH—N=N—,

—N=CH—CH=N—,

—CH=CH—$CH_2$—,

—CH=CH—CH=CH— or

—CH=CH—NR— where R in the above-mentioned groups NR is in each case H or $(C_1-C_4)$alkyl, $(X')_m$ is m substituents X' where the X' in each case independently of one another are halogen, $(C_1-C_6)$ alkyl, $(C_2-C_6)$alkenyl, $(C_2-C_6)$alkynyl, $(C_1-C_6)$ alkoxy, $(C_2-C_6)$alkenyloxy, $(C_2-C_6)$alkynyloxy, $[(C_1-C_4)$alkyl]carbonyl, $[(C_1-C_4)$alkoxy]carbonyl or $[(C_1-C_4)$alkylthio]-carbonyl, the hydrocarbon-containing moieties in the last-mentioned 9 radicals being unsubstituted or substituted, or the oxo group, $(X)_n$ is n substituents X where the X in each case independently of one another are halogen, nitro, cyano, $(C_1-C_6)$alkyl, $(C_2-C_6)$alkenyl, $(C_2-C_6)$ alkynyl $(C_1-C_6)$alkoxy, $(C_2-C_6)$alkenyloxy, $(C_2-C_6)$ alkynyloxy, $[(C_1-C_4)$alkyl]carbonyl, $[(C_1-C_4)$alkoxy]carbonyl or $[(C_1-C_4)$alkylthio]carbonyl, where the hydrocarbon-containing moieties in the last-mentioned 9 radicals are unsubstituted or substituted, or a radical of the formula —$B^3$—$Y^3$, where $B^3$ and $Y^3$ are as defined below, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$alkyl and oxo, $B^1, B^2, B^3$ in each case independently of one another are a direct bond or a divalent group of the formula —O—, —S(O)$_p$—, —S(O)$_p$—O—, —O—S(O)$_p$—, —CO—, —O—CO—, —CO—O—, —NR'—, —O—NR'—, —NR'—O—, —NR'—CO— or —CO—NR'—, where p=0, 1 or 2 and R' is hydrogen, alkyl having 1 to 6 carbon atoms, phenyl, benzyl, cycloalkyl having 3 to 6 carbon atoms or alkanoyl having 1 to 6 carbon atoms, $Y^1, Y^2$ in each case independently of one another are H or an acyclic hydrocarbon radical or a cyclic hydrocarbon radical having 3 to 8 carbon atoms, or a heterocyclic ring having 3 to 9 ring atoms and one hetero atom selected from the group consisting of N, O and S, or a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, each of the hydrocarbon, cyclic hydrocarbon and heterocyclic radicals being unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, hydroxyl, amino, nitro, carboxy, cyano, azido, $[(C_1-C_4)$alkoxy]carbonyl, $[(C_1-C_4)$alkyl]carbonyl, formyl, carbamoyl, mono- and di-$[(C_1-C_4)$alkyl]aminocarbonyl, mono- and di-$[(C_1-C_4)$alkyl]amino, $(C_1-C_4)$alkanoylamino, benzoylamino, $(C_1-C_4)$alkylsulfinyl, $(C_1-C_4)$haloalkylsulfinyl, $(C_1-C_4)$alkylsulfonyl and $(C_1-C_4)$haloalkylsulfonyl, $Y^3$ is $(C_3-C_6)$cycloalkyl which is unsubstituted or substituted by radicals selected from the group consisting of $(C_1-C_4)$alkyl and $(C_1-C_4)$haloalkyl, or phenyl which is unsubstituted or substituted by radicals selected from the group consisting of halogen, $(C_1-C_4)$alkyl, $(C_1-C_4)$haloalkyl and $(C_1-C_4)$alkoxy, m is an integer from zero up to the number of the hydrogen atoms in the skeleton of the divalent bridge, n is 0, 1, 2, 3 or 4.

2. A compound of the formula (I) or a salt thereof as claimed in claim 1, wherein $R^1$ is $(C_1-C_4)$alkyl, which is unsubstituted or substituted by one or more radicals selected from the group consisting of halogen, $(C_1-C_4)$alkoxy, $(C_1-C_4)$alkylthio, $(C_1-C_4)$alkylsulfonyl, phenyl which is unsubstituted or substituted by one or more radicals selected from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, amino, mono- and di$[(C_1-C_4)$alkyl]amino, $(C_1-C_4)$alkanoylamino, benzoylamino, nitro, cyano, $[(C_1-C_4)$alkyl]carbonyl, formyl, carbamoyl, mono- and di$[(C_1-C_4)$alkyl]aminocarbonyl and $(C_1-C_4)$alkylsulfonyl, and $(C_3-C_9)$cycloalkyl which is unsubstituted or substituted by one or more radicals $(C_1-C_4)$alkyl, and a heterocyclic ring having 3 to 6 ring atoms and one hetero atom selected from the group consisting of N, O and S and heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, each heterocyclic ring being unsubstituted or substituted by one or more radicals selected from the group consisting of halogen, $(C_1-C_4)$alkyl and oxo, or is $(C_3-C_7)$cycloalkyl, $(C_3-C_7)$cycloalkenyl or a heterocyclic ring having 3 to 6 ring atoms and one hetero atom selected from the group consisting of N, O and S, or a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, the cycloalkyl, cycloalkenyl or heterocyclic radical in each case being unsubstituted or substituted by one or more radicals selected from the group consisting of halogen, nitro, cyano, thiocyanato and a radical of the formula $B^1$—$Y^1$, where $B^1$ and $Y^1$ are as defined further below, wherein a pair of substituents optionally forms a fused benzene, or a fused or spirolinked ring selected from the group consisting of $(C_3-C_7)$cycloalkyl, $(C_3-C_7)$cycloalkenyl and a heterocyclic ring having 3 to 6 ring atoms and one hetero atom selected from the group consisting of N, O and S, the benzene, cycloalkyl, cycloalkenyl or heterocyclic ring being unsubstituted or substituted by one or more radicals selected from the group consisting of halogen, $(C_1-C_4)$alkyl, $(C_1-C_4)$haloalkyl and oxo, or is phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, hydroxyl, amino, nitro, carboxy, cyano, azido, $[(C_1-C_4)$alkoxy]carbonyl, $[(C_1-C_4)$alkyl]carbonyl, formyl, carbamoyl, mono- and di-$[(C_1-C_4)$alkyl]aminocarbonyl, mono- and di-$[(C_1-C_4)$alkyl]amino, $(C_1-C_4)$alkanoylamino, benzoylamino, $(C_1-C_4)$alkylsulfinyl, $(C_1-C_4)$haloalkylsulfinyl, $(C_1-C_4)$alkylsulfonyl and $(C_1-C_4)$haloalkylsulfonyl, $R^2$ and $R^3$ in each case independently of one another are hydrogen, amino or alkylamino or dialkylamino, each of which has 1 to 4 carbon atoms in the alkyl radical, an acyclic or cyclic hydrocarbon radical or hydrocarbon-oxy radical, each of which has 1 to 6 carbon atoms, or a heterocyclyl radical, heterocyclyloxy radical or heterocyclylamino radical, each of which has 3 to 6 ring atoms and one hetero ring atom selected from the group consisting of N, O and S, where each of the five last-mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, or $R^2$ and $R^3$ together with the nitrogen atom of the group $NR^2R^3$ are a heterocyclic radical having 3 to 6 ring atoms and one hetero atom selected from the group consisting of N, O and S or are piperazinyl or morpholinyl, and the radical is unsubstituted or substituted by one or more radicals selected from the group consisting of halogen, $(C_1-C_4)$alkyl, $(C_1-C_4)$haloalkyl and oxo, $R^4$ is hydrogen, amino, alkylamino or dialkylamino, each of which has 1 to 6 carbon atoms in the alkyl radical, an acyclic or cyclic hydrocarbon radical or hydrocarbon-oxy radical each of which has 1 to 6 carbon atoms, or a heterocyclyl, heterocyclyloxy or heterocyclylamino, the heterocyclyl portion in each case is a heterocyclic radical heterocyclic ring having 3 to 6 ring atoms and one hetero atom selected from the group consisting of N, O and S, or is a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, each of the hydrocarbon, hydrocarbonoxy, heterocyclyl, heterocyclyloxy or heterocyclylamino radicals are unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or an acyl radical, $R^5$ is hydrogen, nitro, cyano, thiocyanato or a radical of the formula $-B^2-Y^2$, where $B^2$ and $Y^2$ are as defined further below, A-Z is a divalent bridge of the formula
—$(CH_2)_a$—, where a is the integer 2, 3 or 4,
—$W^1$—$(CH_2)_b$—$W^2$—, where b is the integer 1 or 2 and $W^1$, $W^2$ independently of one another are S or O,
—$CH_2CH_2CH_2$—$W^3$—, where $W^3$ is NR, O or S,
—$W^4$—CH=CH—$W^5$—, where $W^4$, $W^5$ independently of one another are S or O,
—CH=CH—$CH_2$—$W^6$—, where $W^6$ is a group of the formula S or O, or
—$CH_2CH_2NR$—,
—$W^7$—CH=N—, where $W^7$ is a group NR, O or S,
—$W^8CH_2$—N=N—, where $W^8$ is a group NR, O or S,
—CH=CH—N=N—,
—N=CH—CH=N—,
—CH=CH—$CH_2$—,
—CH=CH—CH=CH— or
—CH=CH—NR—
where R in the groups NR is in each case H, methyl or ethyl, $(X')_m$ is m substituents X' where the X' in each case independently of one another are halogen, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $[(C_1-C_4)$alkyl]carbonyl, $[(C_1-C_4)$alkoxy]carbonyl or $[(C_1-C_4)$alkylthio]carbonyl, the hydrocarbon-containing moieties in the last-mentioned 9 radicals being unsubstituted or substituted by one or more radicals selected from the group consisting of halogen, $(C_1-C_4)$alkoxy and $(C_1-C_4)$alkylthio, or the oxo group, $(X)_n$ is n substituents X where the X in each case independently of one another are halogen, nitro, cyano, $(C_1-C_6)$alkyl, $(C_1-C_6)$alkoxy, $(C_1-C_4)$alkylcarbonyl, $(C_1-C_4)$alkyloxycarbonyl or $(C_1-C_4)$alkylthiocarbonyl, the last-mentioned five radicals being unsubstituted or substituted by halogen or $(C_1-C_4)$alkoxy, a radical of the formula $-B^3-Y^3$, where $B^3$ and $Y^3$ are as defined below, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$alkyl and oxo, $B^1, B^2$ and $B^3$ in each case independently of one another are a direct bond or a divalent group of the formula —O—, —S—, —CO—, —O—CO—, —CO—O—, —NR'—, —NR'—CO— or —CO—NR'—, where R' is H or $(C_1-C_4)$alkyl, $Y^1$ and $Y^2$ in each case independently of one another are H or an acyclic hydrocarbon radical having 1 to 6 carbon atoms, a cyclic hydrocarbon radical having 3 to 6 carbon atoms or a heterocyclic ring having 3 to 9 ring atoms and one hetero atom selected from the group consisting of N, O and S, or a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, each of the hydrocarbon, cyclic hydrocarbon and heterocyclic radicals being unsubstituted or substituted by one or more radicals selected from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and dialkylamino, nitro, carboxyl, cyano, azido, $[(C_1-C_4)$alkoxy]carbonyl, $[(C_1-C_4)$alkyl]carbonyl, formyl, carbamoyl, mono- and di$[(C_1-C_4)$alkyl]aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, $Y^3$ is $(C_3-C_6)$cycloalkyl which is unsubstituted or substituted by radicals selected from the group consisting of $(C_1-C_4)$alkyl and $(C_1-C_4)$haloalkyl, or phenyl which is unsubstituted or substituted by radicals selected from the group consisting of halogen, $(C_1-C_4)$alkyl, $(C_1-C_4)$haloalkyl and $(C_1-C_4)$alkoxy, m is 0, 1 or 2, and n is 0, 1, 2, 3 or 4.

3. A compound of the formula (I) or a salt thereof as claimed in claim 1, wherein $R^1$ is $(C_1-C_4)$ alkyl,
which is unsubstituted or substituted by one or more radicals selected from the group consisting of halogen, $(C_1-C_4)$alkoxy, $(C_1-C_4)$alkylthio and phenyl which is unsubstituted or substituted by one or more radicals selected from the group consisting of halogen, $(C_1-C_4)$ alkyl and $(C_1-C_4)$haloalkyl, $(C_1-C_4)$alkoxy, $(C_1-C_4)$haloalkoxy, $(C_1-C_4)$alkylthio, nitro, cyano, $[(C_1-C_2)$alkyl]carbonyl, formyl, carbamoyl, mono- and di$[(C_1-C_2)$alkyl]aminocarbonyl, $(C_1-C_4)$alkylsulfonyl and $(C_3-C_7)$cycloalkyl which is unsubstituted or substituted by one or more radicals $(C_1-C_4)$alkyl, or is $(C_3-C_7)$cycloalkyl or a heterocyclic ring having 3 to 6 ring atoms and one hetero atom selected from the group consisting of N, O and S, or a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, the cycloalkyl or heterocyclic radical in each case being unsubstituted or substituted by one or more radicals selected from the group consisting of halogen, nitro, cyano, thiocyanato and a radical of the formula $B^1$—$Y^1$, $B^1$—$Y^1$ being as defined further below, and/or having substituents which, in pairs, can form a spiro-linked ring selected from the $(C_3$–$C_7)$cycloalkyl group which is unsubstituted or substituted by one or more radicals selected from the group consisting of halogen, $(C_1$–$C_4)$alkyl, $(C_1$–$C_4)$haloalkyl and oxo, $R^2$ and $R^3$ independently of one another are hydrogen, amino, formyl, $(C_1$–$C_4)$alkyl, cyano$(C_1$–$C_4)$alkyl, $(C_1$–$C_4)$alkylamino, di [$(C_1$–$C_4)$alkyl]-amino, halo $(C_1$–$C_4)$alkyl, hydroxy$(C_1$–$C_4)$alkyl, $(C_1$–$C_4)$alkoxy-$(C_1$–$C_4)$alkyl, halo$(C_1$–$C_4)$alkoxy-$(C_1$–$C_4)$alkyl, $(C_2$–$C_6)$alkenyl, halo$(C_2$–$C_6)$alkenyl, $(C_2$–$C_6)$alkynyl, halo-$(C_2$–$C_6)$alkynyl, $(C_1$–$C_4)$alkylamino-$(C_1$–$C_4)$alkyl, di [$(C_1$–$C_4)$alkyl]-amino-$(C_1$–$C_4)$alkyl, $(C_3$–$C_9)$cycloalkylamino-$(C_1$–$C_4)$alkyl, $(C_3$–$C_9)$cycloalkyl, $(C_3$–$C_9)$heterocyclyl-$(C_1$–$C_4)$alkyl, the cyclic groups in the last-mentioned 3 radicals being unsubstituted or substituted by one or more radicals selected from the group consisting of $(C_1$–$C_4)$alkyl, halogen and cyano, or phenyl, phenoxy, phenylcarbonyl, phenoxycarbonyl, phenylcarbonyl-$(C_1$–$C_4)$alkyl, $(C_1$–$C_4)$alkoxycarbonyl-$(C_1$–$C_4)$alkyl, $(C_1$–$C_4)$alkylaminocarbonyl-$(C_1$–$C_4)$alkyl, $(C_1$–$C_4)$alkylcarbonyl, $(C_1$–$C_4)$alkoxycarbonyl, aminocarbonyl, $(C_1$–$C_4)$alkylaminocarbonyl, phenoxy-$(C_1$–$C_4)$alkyl, phenyl-$(C_1$–$C_4)$alkyl, heterocyclyl, heterocyclylamino, heterocyclyloxy, heterocyclylthio, or one of the last-mentioned 17 radicals which is substituted in the acyclic moiety or in the cyclic moiety by one or more radicals selected from the group consisting of halogen, nitro, cyano, $(C_1$–$C_4)$alkyl, $(C_1$–$C_4)$alkoxy, $(C_1$–$C_4)$alkylthio, $(C_1$–$C_4)$haloalkyl, $(C_1$–$C_4)$haloalkoxy, formyl, $(C_1$–$C_4)$alkylcarbonyl, $(C_1$–$C_4)$alkoxycarbonyl and $(C_1$–$C_4)$alkoxy, heterocyclyl, where the term heterocyclyl used above alone or in combinations being a heterocyclic ring having one hetero atom selected from the group consisting of N, O and S or being a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, $R^2$ and $R^3$ together with the nitrogen atom of the group $NR^2R^3$ are a heterocyclic radical having 3 to 6 ring atoms and one hetero atom selected from the group consisting of N, O and S or are piperazinyl or morpholinyl, and the radical is unsubstituted or substituted by one or more radicals selected from the group consisting of halogen, $(C_1$–$C_4)$alkyl, $(C_1$–$C_4)$haloalkyl and oxo, $R^4$ is hydrogen, amino, formyl, $(C_1$–$C_4)$alkyl, cyano-$(C_1$–$C_4)$alkyl, $(C_1$–$C_4)$alkylamino, di [$(C_1$–$C_4)$alkyl] amino, halo-$(C_1$–$C_4)$alkyl, hydroxy-$(C_1$–$C_4)$alkyl, $(C_1$–$C_4)$alkoxy-$(C_1$–$C_4)$alkyl, halo$(C_1$–$C_4)$alkoxy-$(C_1$–$C_4)$alkyl, $(C_2$–$C_6)$alkenyl, halo-$(C_2$–$C_6)$alkenyl, $(C_2$–$C_6)$alkynyl, halo-$(C_2$–$C_6)$alkynyl, $(C_1$–$C_4)$ alkylamino-$(C_1$–$C_4)$alkyl, di[$(C_1$–$C_4)$alkyl]amino-$(C_1$–$C_4)$alkyl, $(C_3$–$C_9)$cycloalkylamino-$(C_1$–$C_4)$alkyl, $(C_3$–$C_9)$cycloalkyl, $(C_3$–$C_9)$heterocyclyl-$(C_1$–$C_4)$alkyl having 3 to 9 ring members, the cyclic groups in the last-mentioned 3 radicals being unsubstituted or substituted by one or more radicals selected from the group consisting of $(C_1$–$C_4)$alkyl, halogen and cyano, or phenyl, phenoxy, phenylcarbonyl, phenoxycarbonyl, phenylcarbonyl-$(C_1$–$C_4)$alkyl, $(C_1$–$C_4)$alkoxycarbonyl-$(C_1$–$C_4)$alkyl, $(C_1$–$C_4)$alkylaminocarbonyl-$(C_1$–$C_4)$alkyl, $(C_1$–$C_4)$alkylcarbonyl, $(C_1$–$C_4)$alkoxycarbonyl, aminocarbonyl, $(C_1$–$C_4)$alkylaminocarbonyl, phenoxy-$(C_1$–$C_4)$alkyl, phenyl-$(C_1$–$C_4)$alkyl, heterocyclyl, heterocyclylamino, heterocyclyloxy, heterocyclylthio, or one of the last-mentioned 17 radicals which is substituted in the acyclic moiety or in the cyclic moiety by one or more radicals selected from the group consisting of halogen, nitro, cyano, $(C_1$–$C_4)$alkyl, $(C_1$–$C_4)$alkoxy, $(C_1$–$C_4)$alkylthio, $(C_1$–$C_4)$haloalkyl, $(C_1$–$C_4)$haloalkoxy, formyl, $(C_1$–$C_4)$alkylcarbonyl, $(C_1$–$C_4)$alkoxycarbonyl, $(C_1$–$C_4)$alkoxy, heterocyclyl, where the term heterocyclyl used above alone or in combinations being a heterocyclic ring having one hetero atom selected from the group consisting of N, O and S or being a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, $R^5$ is hydrogen, $(C_1$–$C_4)$alkyl, $(C_1$–$C_4)$haloalkyl or $(C_3$–$C_7)$cycloalkyl, A-Z is a divalent bridge of the formula

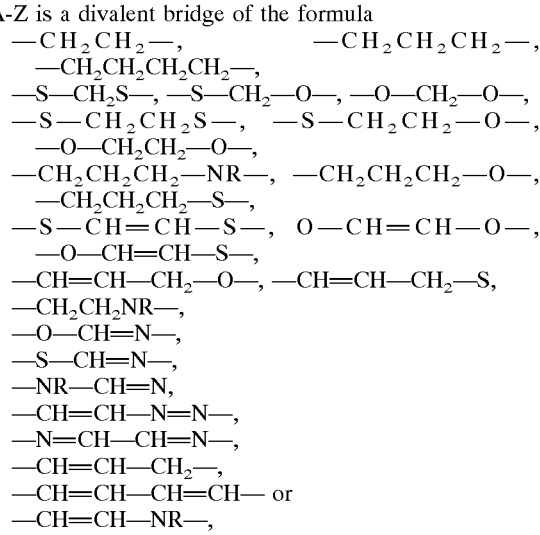

where R in the groups NR is in each case H or methyl, $(X')_m$ is m substituents X' where the X' in each case independently of one another are halogen, $(C_1$–$C_4)$ alkyl, $(C_2$–$C_4)$alkenyl, $(C_2$–$C_4)$alkynyl, $(C_1$–$C_4)$ alkoxy, $(C_2$–$C_4)$alkenyloxy, $(C_2$–$C_4)$alkynyloxy, [$(C_1$–$C_4)$alkyl]carbonyl, [$(C_1$–$C_4)$alkoxy]carbonyl or [$(C_1$–$C_4)$alkylthio]-carbonyl, the hydrocarbon-containing moieties in the last-mentioned 9 radicals being unsubstituted or substituted by one or more radicals selected from the halogen group, or are the oxo group, $(X)_n$ is n substituents X where the X in each case independently of one another are halogen, hydroxyl, amino, nitro, formyl, carboxyl, cyano, thiocyanato, $(C_1$–$C_4)$alkyl, cyano$(C_1$–$C_4)$alkyl, $(C_1$–$C_4)$alkoxy, $(C_1$–$C_4)$alkylamino, di[$(C_1$–$C_4)$alkyl]amino, halo $(C_1$–$C_4)$alkyl, hydroxy-$(C_1$–$C_4)$alkyl, $(C_1$–$C_4)$alkoxy-$(C_1$–$C_4)$alkyl, halo$(C_1$–$C_4)$alkoxy-$(C_1$–$C_4)$alkyl, $(C_1$–$C_4)$alkylthio, halo$(C_1$–$C_4)$alkylthio, $(C_2$–$C_6)$ alkenyl, halo$(C_2$–$C_6)$alkenyl, $(C_2$–$C_6)$alkynyl, halo $(C_2$–$C_6)$alkynyl, $(C_1$–$C_4)$alkylamino-$(C_1$–$C_4)$alkyl, di [$(C_1$–$C_4)$alkyl]amino-$(C_1$–$C_4)$alkyl, $(C_3$–$C_9)$ cycloalkylamino-$(C_1$–$C_4)$alkyl, $(C_3$–$C_9)$cycloalkyl, heterocyclyl-($C_1$–$C_4$)alkyl having 3 to 9 ring members, the cyclic groups in the last-mentioned 3 radicals being unsubstituted or substituted by one or more radicals selected from the group consisting of ($C_1$–$C_4$)alkyl, halogen and cyano, or phenyl, phenoxy, phenylcarbonyl, phenoxycarbonyl, phenylcarbonyl-($C_1$–$C_4$)alkyl, ($C_1$–$C_4$)alkoxycarbonyl-($C_1$–$C_4$)alkyl, ($C_1$–$C_4$)alkylaminocarbonyl-($C_1$–$C_4$)alkyl, ($C_1$–$C_4$)alkylcarbonyl, ($C_1$–$C_4$)alkoxycarbonyl, aminocarbonyl, ($C_1$–$C_4$)alkylaminocarbonyl, phenoxy-($C_1$–$C_4$)alkyl, phenyl-($C_1$–$C_4$)alkyl, heterocyclyl, heterocyclylamino, heterocyclyloxy, heterocyclylthio or one of the last-mentioned 17 radicals which is substituted in the acyclic moiety or in the cyclic moiety by one or more radicals selected from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl and ($C_1$–$C_4$)alkoxy, heterocyclyl, where the term heterocyclyl used above alone or in combinations being a heterocyclic ring having one hetero atom selected from the group consisting of N, O and S or being a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, ($C_1$–$C_4$)alkyl and oxo, $B^1$ is a direct bond or a divalent group of the formula —O—, —S—, —CO—, —O—CO—, —CO—O—, —NR'—, —NR'—CO— or —CO—NR'—, where R' is H or ($C_1$–$C_4$)alkyl, $Y^1$ is H or an acyclic hydrocarbon radical having 1 to 4 carbon atoms, a cyclic hydrocarbon radical having 3 to 6 carbon atoms or a heterocyclic ring having 3 to 6 ring atoms and one hetero atom selected from the group consisting of N, O and S, or a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, each of the acyclic hydrocarbon, cyclic hydrocarbon and heterocyclic radicals being unsubstituted or substituted by one or more radicals selected from the group consisting of halogen, ($C_1$–$C_4$)alkoxy, ($C_1$–$C_4$)haloalkoxy, ($C_1$–$C_4$)alkylthio, hydroxyl, amino, mono- and dialkylamino, [($C_1$–$C_4$)alkoxy]carbonyl, [($C_1$–$C_4$)alkyl]carbonyl, formyl, carbamoyl, mono- and di [($C_1$–$C_4$)alkyl]aminocarbonyl, ($C_1$–$C_4$)alkylsulfinyl, ($C_1$–$C_4$)haloalkylsulfinyl, ($C_1$–$C_4$)alkylsulfonyl, ($C_1$–$C_4$)haloalkylsulfonyl and, in the case of cyclic radicals, also ($C_1$–$C_4$)alkyl and ($C_1$–$C_4$)haloalkyl.

4. A compound of the formula (I) or a salt thereof as claimed in claim 1, wherein $R^1$ is ($C_1$–$C_4$)alkyl, ($C_1$–$C_4$)haloalkyl, benzyl, [($C_3$–$C_6$)cycloalkyl]-($C_1$–$C_2$)-alkyl, ($C_3$–$C_6$)cycloalkyl or a heterocyclic ring having 3 to 6 ring atoms and one hetero atom selected from the group consisting of N, O and S, or a heterocyclic ring selected from the group consisting of pyrimidinyl, pyridazinyl, pyrazinyl, thiazolyl, oxazolyl, pyrazolyl, imidazolyl, piperazinyl, dioxolanyl and morpholinyl, each of the cycloalkyl or heterocyclic radicals being unsubstituted or substituted by one or more radicals selected from the group consisting of halogen, nitro, cyano, thiocyanato and a radical of the formula $B^1$—$Y^1$, where $B^1$ and $Y^1$ are as defined further below, and/or having substituents which, in pairs, can form a spiro-linked ring selected from the ($C_3$–$C_7$)cycloalkyl group which is unsubstituted or substituted by one or more radicals selected from the group consisting of halogen, ($C_1$–$C_4$)alkyl, ($C_1$–$C_4$)haloalkyl and oxo, $R^2$ and $R^3$ independently of one another are hydrogen, amino, formyl, ($C_1$–$C_4$)alkyl, ($C_1$–$C_4$)alkoxy-($C_1$–$C_4$)alkyl, ($C_3$–$C_6$)alkenyl, ($C_3$–$C_6$)alkynyl, ($C_1$–$C_4$)alkylamino-($C_1$–$C_4$)alkyl, di[($C_1$–$C_4$)alkyl]-amino-($C_1$–$C_4$)alkyl or phenyl, phenyl-($C_1$–$C_4$)alkyl, phenylcarbonyl or phenoxycarbonyl or one of the last-mentioned four radicals which is up to trisubstituted in the phenyl moiety by radicals selected from the group consisting of halogen, ($C_1$–$C_4$)alkyl, ($C_1$–$C_4$)alkoxy and ($C_1$–$C_4$)alkoxycarbonyl, or $R^2$ and $R^3$ together with the nitrogen atom of the group $NR^2R^3$ are a heterocyclic radical having 3 to 6 ring atoms and one hetero atom selected from the group consisting of N, O and S or are piperazinyl or morpholinyl, and the radical is unsubstituted or substituted by one or more radicals selected from the group consisting of halogen, ($C_1$–$C_4$)alkyl, ($C_1$–$C_4$)haloalkyl and oxo, $R^4$ is hydrogen, amino, formyl, ($C_1$–$C_4$)alkyl, di[($C_1$–$C_4$)alkyl]amino, ($C_1$–$C_4$)alkoxy-($C_1$–$C_4$)alkyl, ($C_3$–$C_6$)alkenyl, ($C_3$–$C_6$)alkynyl, ($C_1$–$C_4$)dialkylamino-($C_1$–$C_4$)alkyl, phenyl, phenoxy-($C_1$–$C_4$)alkyl, phenyl-($C_1$–$C_4$)alkyl, phenoxycarbonyl, phenylaminocarbonyl or one of the last-mentioned five radicals which is monosubstituted to trisubstituted in the phenyl moiety by radicals selected from the group consisting of halogen, ($C_1$–$C_4$)alkyl, ($C_1$–$C_4$)alkoxy and ($C_1$–$C_4$)alkoxycarbonyl, $R^5$ is hydrogen, ($C_1$–$C_4$)alkyl, ($C_1$–$C_4$)haloalkyl or ($C_3$–$C_7$)cycloalkyl, A-Z is a divalent bridge of the formula
—$CH_2CH_2$—, —$CH_2CH_2CH_2$—,
—$CH_2CH_2CH_2CH_2$—,
—S—$CH_2CH_2$S—, —S—$CH_2CH_2$—O—,
—O—$CH_2CH_2$—O—,
—$CH_2CH_2CH_2$—NR—, —$CH_2CH_2CH_2$—O—,
—$CH_2CH_2CH_2$—S—,
—S—CH=CH—S—, O—CH=CH—O—,
—CH=CH—$CH_2$—O—, —O—CH=CH—S,
—$CH_2CH_2$NR—,
—O—CH=N—,
—S—CH=N—,
—NR—CH=N—,
—CH=CH—N=N—,
—N=CH—CH=N—,
—CH=CH—$CH_2$—,
—CH=CH—CH=CH— or
—CH=CH—NR,
where R in the groups NR is in each case H or methyl, $(X')_m$ is m substituents X' where the X' in each case independently of one another are halogen, ($C_1$–$C_4$)alkyl or ($C_1$–$C_4$)alkoxy, $(X)_n$ is n substituents X where the X in each case independently of one another are halogen, hydroxyl, ($C_1$–$C_4$)alkyl or ($C_1$–$C_4$)alkoxy, $B^1$ is a direct bond or a divalent group of the formula —O—, —S— or —O—CO—, Y¹ is H, $(C_1-C_4)$alkyl, $(C_3-C_6)$cycloalkyl or phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, mono- and dialkylamino.

5. A compound of the formula (I) or a salt thereof as claimed in claim 1, wherein R¹ is $(C_1-C_4)$alkyl, $(C_1-C_4)$haloalkyl or $[(C_3-C_6)$cycloalkyl]methyl, R² and R³ independently of one another are hydrogen, formyl or $(C_1-C_4)$alkyl or R² and R³ together with the nitrogen atom of the group NR²R³ are a heterocyclic radical having 3 to 6 ring atoms and one hetero atom selected from the group consisting of N, O and S or are piperazinyl or morpholinyl, and the radical is unsubstituted or substituted by one or more radicals selected from the group consisting of halogen, $(C_1-C_4)$alkyl, $(C_1-C_4)$haloalkyl and oxo, R⁴ is hydrogen or $(C_1-C_4)$alkyl, R⁵ is H or $(C_1-C_4)$alkyl, A-Z is a divalent bridge of the formula
—CH₂CH₂—, CH₂CH₂CH₂—,
—CH₂CH₂CH₂CH₂—,
—S—CH₂CH₂S, —O—CH₂CH₂—O—,
—CH₂CH₂CH₂—NR—, —CH₂CH₂CH₂—O—,
—CH₂CH₂CH₂—S—,
—CH₂CH₂NR—,
—N=CH—O—, —N=CH—S—, —N=CH—NR,
—N=CH—CH=N—,
—CH=CH—CH₂—,
—CH=CH—CH=CH— or
—CH=CH—NR,
where R in the groups NR is in each case H or methyl, $(X')_m$ is m substituents X' where the X' in each case independently of one another are halogen or $(C_1-C_4)$alkyl, and $(X)_n$ is n substituents X where the X in each case independently of one another are halogen, hydroxyl, $(C_1-C_4)$alkyl or $(C_1-C_4)$alkoxy.

6. A compound of the formula (1) or a salt thereof as claimed in claim 1, wherein A-Z is —(CH₂)ₐ—, where a is the integer 2, 3, or 4.

7. A compound as claimed in claim 1, wherein the compound is of the formula (Ia),

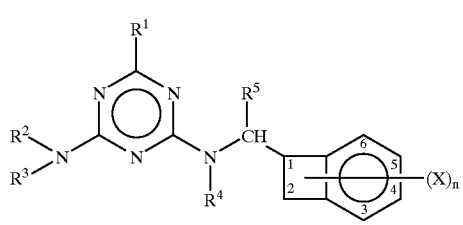

(Ia)

in which R¹, R², R³, R⁴, R⁵, X and n are defined as in formula (I), or a salt thereof.

8. A compound as claimed in claim 1, wherein the compound is of the formula (Ib),

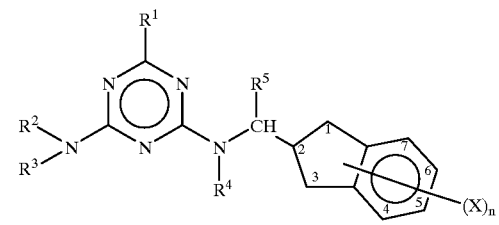

(Ib)

in which R¹, R², R³, R⁴, R⁵, X and n are defined as in formula (I), or a salt thereof.

9. A compound as claimed in claim 1, wherein the compound is of the formula (Ic),

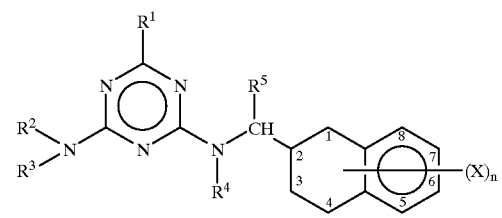

(Ic)

in which R¹, R², R³, R⁴, R⁵, X and n are defined as in formula (I), or a salt thereof.

10. A compound as claimed in claim 1, wherein the compound is of the formula (Ie),

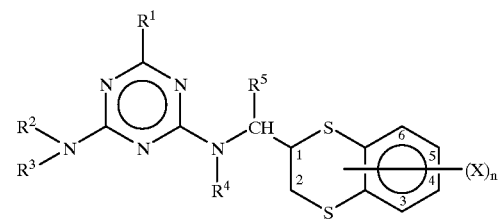

(Ie)

in which R¹, R², R³, R⁴, R⁵, X and n are defined as in formula (I), or a salt thereof.

11. A compound as claimed in claim 1, wherein the compound is of the formula (If),

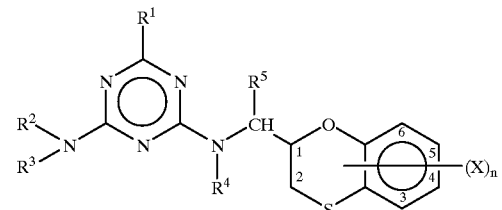

(If)

in which R¹, R², R³, R⁴, R⁵, X and n are defined as in formula (I), or a salt thereof.

12. A compound as claimed in claim 1, wherein the compound is of the formula (Ig),

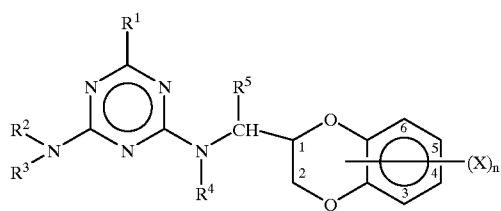
(Ig)

in which $R^1$, $R^2$, $R^3$, $R^4_1$ $R^5$, X and n are defined as in formula (I), or a salt thereof.

13. A compound as claimed in claim 1, wherein the compound is of the formula (Ih),

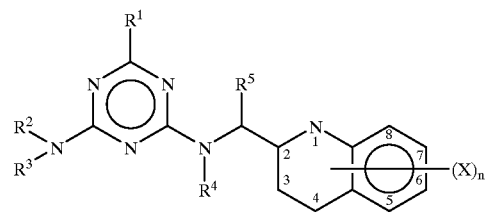
(Ih)

in which $R^1$, $R^2$, $R^3_1$ $R^4_1$ $R^5$, X and n are defined as in formula (I), or a salt thereof.

14. A compound as claimed in claim 1, wherein the compound is of the formula (Ij),

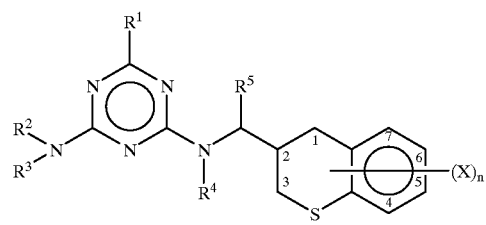
(Ij)

in which $R^1$, $R^2$, $R^3$, $R^4$, $R^5$, X and n are defined as in formula (I) or a salt thereof.

15. A compound as claimed in claim 1, wherein the compound is of the formula (Ik),

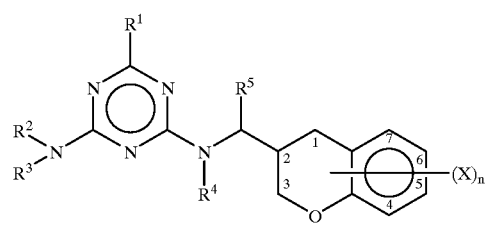
(Ik)

in which $R^1$, $R^2$, $R^3$, $R^4$, $R^5$, X and n are defined as in formula (I), or a salt thereof.

16. A compound as claimed in claim 1, wherein the compound is of the formula (Il),

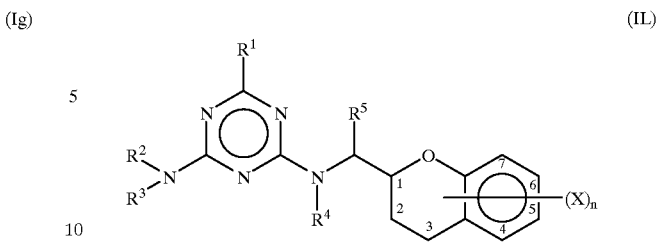
(Il)

in which $R^1$, $R^2$, $R^3$, $R^4$, $R^5$, X and n are defined as in formula (I), or a salt thereof.

17. A compound as claimed in claim 1, wherein the compound is of the formula (Im),

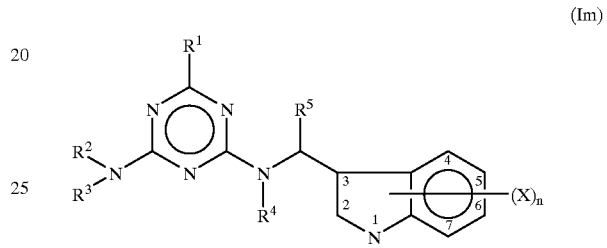
(Im)

in which $R^1$, $R^2$, $R^3$, $R^4$, $R^5$, X and n are defined as in formula (I), or a salt thereof.

18. A compound as claimed in claim 1, wherein the compound is of the formula (In),

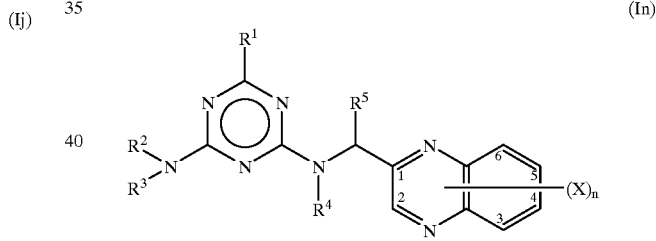
(In)

in which $R^1$, $R^2_1$ $R^3$, $R^4$, $R^5$, X and n are defined as in formula (I), or a salt thereof.

19. A compound as claimed in claim 1, wherein the compound is of the formula (Io),

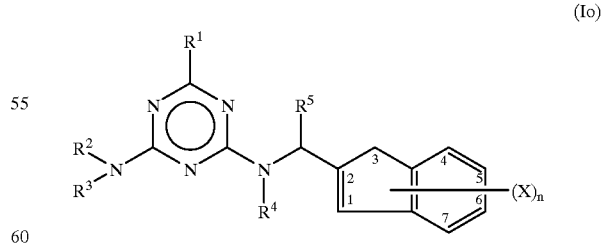
(Io)

in which $R^1$, $R^2$, $R^3$, $R^4$, $R^5$, X and n are defined as in formula (I), or a salt thereof.

20. A compound as claimed in claim 1, wherein the compound is of the formula (Ip), (Ip)

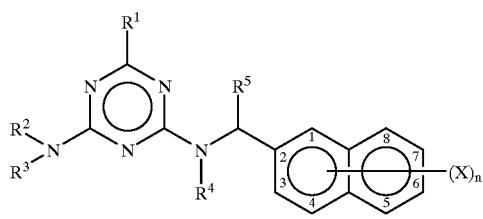

in which R¹, R², R³, R⁴, R⁵, X and n are defined as in formula (I), or a salt thereof.

21. A compound as claimed in claim 1, wherein the compound is of the formula (Iq), (Iq)

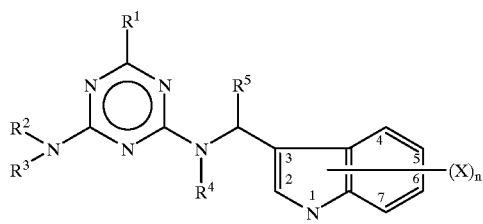

in which R¹, R², R³, R⁴, R⁵, X and n are defined as in formula (I) or a salt thereof.

22. A compound as claimed in claim 1, wherein the compound is of the formula (Ir), (Ir)

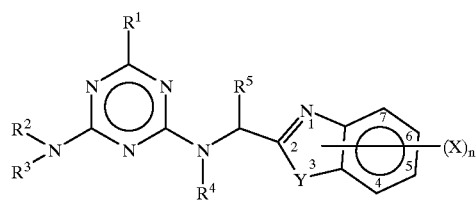

in which R¹, R², R³, R⁴, R⁵, X and n are defined as in formula (I), or a salt thereof.

23. A compound as claimed in claim 1, wherein the compound is of the formula (Is), (Is)

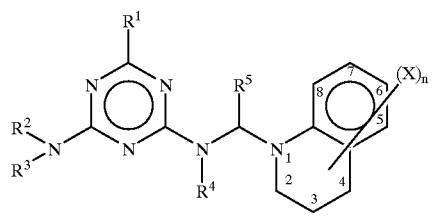

in which R¹, R², R³, R⁴, R⁵, X and n are defined as in formula (I), or a salt thereof.

24. A herbicidal or plant growth-regulating composition, which comprises one or more compounds of the formula (I) or a salt thereof as claimed in claim 1, and formulation auxiliaries conventionally used in crop protection.

25. A method of controlling harmful plants or of regulating the growth of plants, which comprises applying an effective amount of one or more compounds of the formula (I) or a salt thereof as claimed in claim 1, to the plants, the seeds of the plants or the area under cultivation.

* * * * *